United States Patent
George et al.

(10) Patent No.: US 7,202,320 B2
(45) Date of Patent: *Apr. 10, 2007

(54) SILICONE COMPOSITION CROSSLINKABLE INTO ELASTOMER BY HYDROSILYLATION, IN THE PRESENCE OF CARBENE-BASED METAL CATALYSTS, AND CATALYSTS

(75) Inventors: Catherine George, Ecully (FR); Delphine Blanc-Magnard, Lyons (FR); Alain Pouchelon, Meyzheu (FR); Sébastien Sterin, Lyons (FR)

(73) Assignee: Rhodia Chimie, Aubervilliers (FR)

( * ) Notice: Subject to any disclaimer, the term of this patent is extended or adjusted under 35 U.S.C. 154(b) by 129 days.

This patent is subject to a terminal disclaimer.

(21) Appl. No.: 10/479,720

(22) PCT Filed: Jun. 3, 2002

(86) PCT No.: PCT/FR02/01863

§ 371 (c)(1),
(2), (4) Date: May 27, 2004

(87) PCT Pub. No.: WO02/098971

PCT Pub. Date: Dec. 12, 2002

(65) Prior Publication Data

US 2004/0236054 A1    Nov. 25, 2004

(30) Foreign Application Priority Data

Jun. 7, 2001   (FR) .................................. 01 07473

(51) Int. Cl.
*C08G 77/08* (2006.01)
(52) U.S. Cl. ............................ 528/14; 528/15; 528/21; 528/32; 528/31; 502/325
(58) Field of Classification Search ................. 528/15, 528/14, 21, 32, 31; 502/325
See application file for complete search history.

(56) References Cited

U.S. PATENT DOCUMENTS

| 5,278,839 A | 1/1994 | Matsumoto et al. |
| 5,426,200 A | 6/1995 | Dauth et al. |
| 6,803,440 B2 * | 10/2004 | Marko et al. ................. 528/14 |
| 6,815,518 B2 * | 11/2004 | Sterin ............................ 528/15 |

FOREIGN PATENT DOCUMENTS

| EP | 0 061 241 A | | 9/1982 |
| EP | 0 545 591 A | | 6/1993 |
| EP | 545 591 | * | 6/1993 |
| FR | 2 717 481 A | | 9/1995 |
| FR | 2 750 349 A | | 1/1998 |
| FR | 2 801 887 A | | 6/2001 |
| WO | 01/42258 | * | 6/2001 |
| WO | 02/14407 | * | 2/2002 |

OTHER PUBLICATIONS

Herrmann, et al., Angew. Chem. Int. Ed. Engl. (1996), 35, No. 23/24, pp. 2805-2807.*
Dieter Enders et al., "Diastereoselective Synthesis of Chiral (*Triazolinylidene*)*rhodium* Complexes Containing an Axis of Chirality," Eur. J. Inorg. Chem., 1998, pp. 913-919, No. 7, WILEY-VCH Verlag GmbH, D-69451 Weinheim.

* cited by examiner

*Primary Examiner*—Kuo-Liang Peng
(74) *Attorney, Agent, or Firm*—Buchanan, Ingersoll & Rooney PC

(57) ABSTRACT

The invention concerns a silicone composition crosslinkable into elastomer by hydrosilylation, in the presence of carbene-based metal catalysts. The invention aims at providing a composition of that type, stable over long periods at room temperature (one day to several months), without loss of its characteristic of being heat-curable by hydrosilylation and without generating secondary isomerization or coloring reactions. The invention is characterised in that the composition comprises: a polyorganovinylsiloxane(polydimethyl)(methylvinyl) siloxane; a polyorganohydrogenosiloxane; a platinum catalyst formed by a complex of formula C3 and optionally an acetylene crosslinking inhibitor, optionally a siliceous filler. The invention also concerns novel hydrosilylation catalysts of the metal complex type of formula C3 above. The life span of the potted single-constituent compositions of the invention is significantly increased

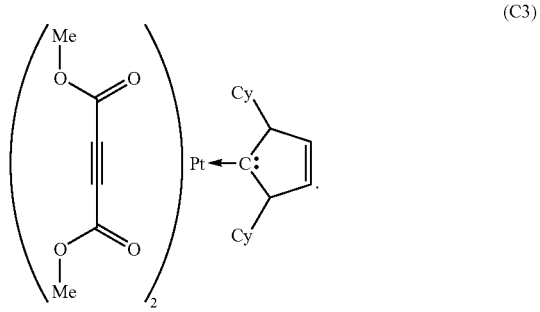
(C3)

38 Claims, No Drawings

SILICONE COMPOSITION CROSSLINKABLE INTO ELASTOMER BY HYDROSILYLATION, IN THE PRESENCE OF CARBENE-BASED METAL CATALYSTS, AND CATALYSTS

The invention relates to the catalysis of hydrosilylation reactions and especially for the hydrosilylation of ethylenically and/or acetylenically unsaturated compounds (for example olefins or acetylenic derivatives), in particular those involving polyorganosiloxanes (POS) bearing Si—H units and POSs bearing Si-(ethylenic or acetylenic unsaturation) units.

More specifically, the invention relates to silicone compositions that are crosslinkable—preferably into elastomers—by hydrosilylation of at least one polyorganosiloxane-A-(POS) bearing ethylenic and/or acetylenic unsaturation(s), using at least one polyorganohydrogenosiloxane -B-, in the presence of a metallic catalyst -C- and optionally comprising at least one inhibitor -D- of the hydrosilylation reaction.

Conventionally, hydrosilylation reactions that allow silicones to crosslink are catalyzed via platinum-catalysts (U.S. Pat. No. 2,823,218, U.S. Pat. No. 2,970,150). In practice, to date, the majority of industrial hydrosilylation reactions are catalyzed with Karstedt solution, which consists of complexes of platinum in oxidation state 0. The ideal general formula of the Karstedt complex is $Pt_2$(tetramethyldivinylsiloxane)$_3$:

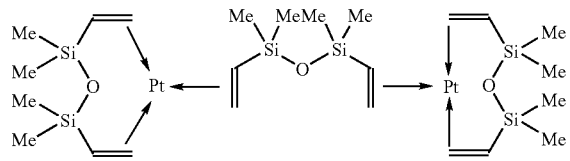

in which Me represents methyl.

The Karstedt complex is prepared by placing 1,3-divinyltetramethyldisiloxane in contact with chloroplatinic acid ($H_2PtCl_6$), in the presence of $NaHCO_3$ and an aqueous-alcoholic solvent (isopropanol).

This common catalyst and its production are described in patent U.S. Pat. No. 3,775,452.

The very high catalytic activity of this type of catalyst, even at room temperature, is a major drawback in the context of its use in EVC polyadditions, since the crosslinking of the elastomer starts as soon as all the components are placed in contact.

Another drawback of this catalyst lies in a possible instability of the catalyst during reaction: the precipitation of metallic platinum and the formation of insoluble colloids in the reaction medium have been observed: this instability of the catalyst in the reaction medium has the effect of reducing the catalytic activity. Furthermore, it results in products that are occasionally colored, which are not particularly appreciated by users.

Another major drawback of the Karstedt catalyst is the concomitant formation of side products of the hydrosilylation reaction: products resulting from isomerization reactions of the olefinic double bond and/or of hydrogenation reactions are isolated along with the hydrosilylation products.

The unpublished patent application FR 99/15432 of Dec. 7, 1999 discloses metallic complexes that are useful as hydrosilylation catalysts, of formula:

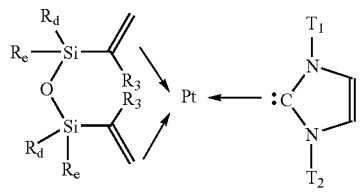

in which:

$R_3$ represents a hydrogen atom; a ($C_1$–$C_8$)alkyl group; or a ($C_3$–$C_8$)cycloalkyl group optionally substituted with ($C_1$–$C_4$)alkyl;

$T_1$ and $T_2$ are identical and represent ($C_1$–$C_8$)alkyl or ($C_3$–$C_8$)cycloalkyl;

$R_d$ and $R_e$ are identical and represent ($C_1$–$C_8$)alkyl or ($C_3$–$C_8$)cycloalkyl;

(preferably, $T_1=T_2=R_d=R_e$=methyl).

These Pt/carbene metallic complexes are obtained according to a two-step methodology illustrated by the following example:

1. Preparation of the Carbene:

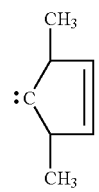

2. Preparation of the Platinum Complex of Formula:

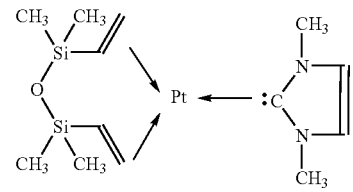

According to this unpublished prior patent application, the catalysts are used to catalyze the reaction of a compound containing an ethylenic double bond or an acetylenic triple bond (unsaturated compound) with a compound containing at least one ≡Si—H unit so as to form a C—Si bond. Examples of compounds containing an ethylenic double bond are ethylene, propylene, 1-butylene, 1-pentene, 2-methyl-1-butene, 1-hexene, 1-heptene, 1-octene, 3-ethyl-1-hexene, 1-decene, 4,4-dimethyl-1-nonene, vinylcyclohexene, styrene and 2-vinylnaphthalene.

Examples of compounds containing an acetylenic triple bond are: ethynyl, 2-propynyl, 1-propynyl and 2-penten-4-ynyl.

Examples of compounds containing at least one ≡Si—H unit are polymethylhydrogenosiloxane, polydimethylsiloxane containing an —SiH end group, methylhydrogenodimethylsiloxane copolymers, methylhydrogenomethyloctylsiloxane copolymers and methylhydrogenocyclosiloxane polymers.

Patent U.S. Pat. No. 5,728,839 also discloses metal/carbene complexes, prepared in two steps from imidazolium, benzimidazolium, triazolium, tetrazolium or pyrazolium salts (for example iodide). These metallic (rhodium) complexes with heterocyclic carbenes are described as possibly being useful as catalysts for the hydrogenation or hydroformylation of unsaturated organic compounds, such as olefins. That US patent does not concern the crosslinking of silicones.

Now, it might be advantageous to have available, in the field of crosslinkable silicones—especially into elastomers—catalysts, that are active at elevated temperature and that show little or no activity at room temperature. This would make it possible to formulate one-component silicones, which are crosslinkable at elevated temperature and stable on storage for long periods at room temperature (pot life). One-component silicone compositions are those comprising in the same mixture all the reactive species (POS Si-vinyl/POS Si—H) and the catalyst. Conventionally, to increase the pot life of one-component silicone compositions, use is made of crosslinking inhibitors. Thus, with the Karstedt catalyst, the use of an inhibitor is imperative and allows the stability at room temperature of a POS Si-vinyl/POS Si—H composition to pass, for example, from 1 minute to 24 hours. However, this is an expensive solution with limited performance qualities, since the use of large amounts of inhibitor is liable to disrupt the behavior of the elastomer during its crosslinking.

With such a state of the art, one of the essential objectives of the invention is to propose a hydrosilylation-crosslinkable silicone composition comprising as catalyst one or more heterocyclic carbene-based metallic complexes, this catalyst having low activity at room temperature, so as to allow the preparation of one-component compositions comprising the catalyst and of compounds capable of reacting at elevated temperature by hydrosilylation of unsaturated units (e.g. POS SiH/POS Si-alkenyl), while at the same time being stable at room temperature for long periods (e.g. from one day to several months).

Another essential objective of the invention is to propose a hydrosilylation-crosslinkable silicone composition comprising as catalyst one or more heterocyclic carbene-based metallic complexes, this composition not being the site, during the crosslinking, of isomerization side reactions or of colorations liable to disrupt the hydrosilylation.

Another essential objective of the invention is to propose novel heterocyclic carbene-based metallic complexes that may be used as hydrosilylation catalysts, these catalysts needing to be stable in the reaction medium, so as to limit the formation:
of undesirable side products resulting from isomerization reactions of the olefinic double bond and/or hydrogenation reactions,
and/or of side products that are the cause of colorations that are just as poorly appreciated.

Another essential objective of the invention is to propose novel heterocyclic carbene-based metallic complexes that may be used as hydrosilylation catalysts, these catalysts needing to produce selective catalytic activity of a high qualitative and quantitative level in the reaction medium.

Another essential objective of the invention is to propose novel heterocyclic carbene-based metallic complexes that may be used as hydrosilylation catalysts, these catalysts needing to be very active at elevated temperature and to have little or no activity at room temperature, so as to be-able to formulate one-component silicone compositions that are crosslinkable at elevated temperature and stable on storage for long periods at room temperature (pot life), and to achieve this with little or no crosslinking inhibitor.

Another essential objective of the invention is to propose a hydrosilylation process, in particular for the hydrosilylation of ethylenically and/or acetylenically unsaturated compounds, in the presence of a catalyst comprising the above-mentioned novel-metallic complexes.

These objectives, among others, are achieved by the present invention, which relates firstly to a hydrosilylation-crosslinkable silicone composition of at least one polyorganosiloxane -A- (POS) bearing ethylenic and/or acetylenic unsaturation(s), using at least one polyorganohydrogenosiloxane -B-, in the presence of a metallic catalyst -C- and optionally comprising at least one inhibitor -D- of the hydrosilylation reaction;

characterized in that the catalyst -C- comprises at least one compound selected from the products of formula (I):

(I)

in which

M represents a metal chosen from the metals of group 8 of the Periodic Table as published in the Handbook of Chemistry and Physics, $65^{th}$ Edition, 1984–1985;

$L_\gamma$ represents a carbene of formula (II):

II in which:
A and B independently represent C or N, it being understood that when A represents N, then $T_4$ represents nothing, and when B represents N, then $T_3$ represents nothing;

$T_3$ and $T_4$ independently represent a hydrogen atom; an alkyl group; a cycloalkyl group optionally substituted with alkyl or alkoxy; an aryl group optionally substituted with alkyl or alkoxy; an alkenyl group; an alkynyl group; or an arylalkyl group in which the aryl portion is optionally substituted with alkyl or alkoxy; or alternatively $T_3$ and $T_4$ may form, together with A and B when these each represent a carbon atom, an aryl;

$T_1$ and $T_2$ independently represent an alkyl group; an alkyl group optionally substituted with alkyl; a perfluorinated alkyl group or an alkyl group optionally substituted with a perfluoroalkyl group; a cycloalkyl group optionally substituted with alkyl or alkoxy; an aryl group optionally substituted with alkyl or alkoxy; an alkenyl group; an alkynyl group; or an arylalkyl group in which the aryl portion is optionally substituted with alkyl or alkoxy; or alternatively $T_1$ and $T_2$ independently represent a monovalent radical of formula (V) below:

$$V_1\text{-}V_2 \qquad (V)$$

in which:
$V_1$ is a divalent hydrocarbon-based radical, preferably an alkylene,
$V_2$ is a monovalent radical chosen from the following group of substituents:
 alkoxy, —OR° with R° corresponding to hydrogen, alkyl or aryl
 amine, preferably $N(R°)_2$ with R° corresponding to hydrogen, alkyl or aryl
$T_1$ and $T_2$ independently represent a monovalent radical of formula (W) below:

$$W_1\text{-}\omega\text{-}W_2 \qquad (W)$$

in which:
$W_1$ is a divalent hydrocarbon-based radical, preferably an optionally substituted linear or branched $C_1$–$C_{10}$ alkylene,
ω represents:

—$R^1C$=$CR^1$— with $R^1$ corresponding to H or alkyl or

—C≡C—

$W_2$ is a monovalent radical chosen from the group of the following substituents
$R^2$=alkyl, H;
Si-alkyl or Si-alkoxy, preferably —$Si(R^3)_3$ with $R^3$=alkyl;
alcohol, preferably —$C(R^4)_2OH$ with $R^4$=H or alkyl;
ketone, preferably:

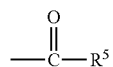

with $R^5$=alkyl;
carboxyl, preferably

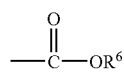

with $R^6$=alkyl;
amide, preferably

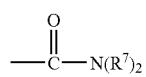

with $R^7$=H, alkyl;
acyl, preferably

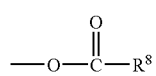

with $R^8$=alkyl;
or alternatively
the substituents $T_1$, $T_2$, $T_3$ and $T_4$ may form in pairs, when they are located on two adjacent ring members in formula (II), a saturated or unsaturated hydrocarbon-based chain;

$L_\alpha$ and $L_\beta$ are ligands that may be identical or different, and each represent:

$$Z^1\text{≡}Z^2 \qquad (III.1)$$

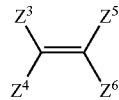 (III.2)

with, in these formulae (III.1) and (III.2):

$Z^1, Z^2, Z^3, Z^4, Z^5, Z^6$ each independently representing:
 a. hydrogen,
 b. a halogen,
 c. a cyano,
 d. a saturated or unsaturated electron-withdrawing hydrocarbon-based group, preferably adjacent to the double or triple bond,
 e. two vicinal $Z^{1\ to\ 6}$ together possibly forming an electron-withdrawing ring advantageously different than the carbene $L_\gamma$ of formula (II) and optionally comprising hetero atoms (preferably O, N or S);
or the substituents $Z^1$ and $Z^2$ together form, in (III.1), a monovalent alkenyl radical comprising at least one electron-withdrawing residue preferably adjacent to the triple bond;
or alternatively $Z^3$ to $Z^6$ form in pairs, in (III.2), a monovalent alkenyl radical comprising at least one electron-withdrawing residue preferably adjacent to the double bond;
or together form the ligand Lδ of formula (IV):

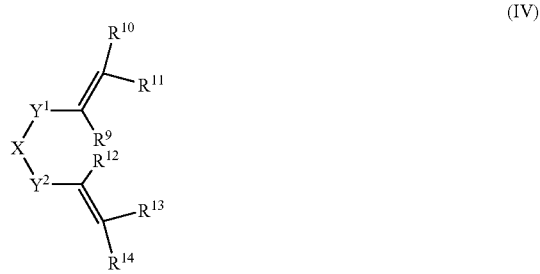

in which:
$Y_1$ and $Y_2$ represent, independently of each other, $CR_aR_b$ or $Si_cR_d$;
X represents O, $NR_e$ or $CR_fR_g$;
$R^{10}$, $R^{11}$, $R^{13}$ and $R^{14}$, which may be identical or different, are chosen from a hydrogen atom, an alkyl group and an aryl group optionally substituted with alkyl;
$R^9$, $R^{12}$, $R_a$, $R_b$, $R_c$ and $R_d$ are chosen independently from a hydrogen atom; an alkyl group; an acyl group; an aryl group optionally substituted with alkyl; a cycloalkyl group optionally substituted with alkyl; and an arylalkyl group in which the aryl portion is optionally substituted with alkyl;
$R_e$ is H or alkyl; or alternatively when $Y_1$ and $Y_2$ independently represent $SiR_cR_d$, two groups $R_c$ linked to two different silicon atoms together form a chain of formula:

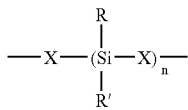

in which n is an integer from 1 to 3; X is as defined above; R and R', which may be identical or different, take any of the meanings given above for $R_e$, it being understood that when n is 2 or 3, only one silicon atom of said chain may be substituted with one or two alkenyl or alkynyl groups; or alternatively when $Y_1$ and $Y_2$ independently represent $SiR_cR_d$, two groups $R_c$ linked to different silicon atoms together form a saturated hydrocarbon-based chain, the two groups $R_c$ together with said silicon atoms and X forming a 6- to 10-membered ring; or alternatively when $Y_1$ and $Y_2$ independently represent $CR_aR_b$, two groups $R_a$ linked to different carbon atoms together form a saturated hydrocarbon-based chain, the two groups $R_a$ together with the carbon atoms that bear them and X form a 6- to 10-membered ring; and $R_f$ and $R_g$ represent, independently of each other, a hydrogen atom; an alkyl group; an acyl group; an aryl group optionally substituted with alkyl; a cycloalkyl group optionally substituted with alkyl; an arylalkyl group in which the aryl portion is optionally substituted with alkyl; a halogen atom; an alkenyl group; an alkynyl group; or a group $SiG_1G_2G_3$ in which $G_1$, $G_2$ and $G_3$ are, independently of each other, alkyl; alkoxy; aryl optionally substituted with alkyl or alkoxy; or arylalkyl in which the aryl portion is optionally substituted with alkyl or alkoxy.

The presence of the specific metal/heterocyclic carbene complexes in the compositions according to the invention give them great stability in ambient atmosphere under normal temperature, humidity and pressure conditions. Such silicone compositions may be stored in one-component form, in the non-crosslinked state, in ambient atmosphere, for very long periods (for example from one to several months). This result is all the more advantageous and surprising since, with certain metal/heterocyclic carbene catalysts, it is possible to dispense with using crosslinking inhibitors or at the very least to use a smaller amount of them, which is entirely beneficial in economic terms and as regards limiting the negative repercussions on the crosslinking of the elastomer and its final qualities.

This stability goes hand in hand with the ability of the compositions according to the invention to crosslink at elevated temperature (for example at and above 100° C.) by hydrosilylation, into elastomers of high quality, especially of high structural and mechanical quality. In addition, the reaction kinetics are satisfactory.

Moreover, no isomerization side reactions and very little undesirable colorations are observed after crosslinking the compositions according to the invention.

These one-component silicone compositions, which have a long shelf life at room temperature, are all the more advantageous since they are not prohibitively expensive. This advantage is even more pronounced when they do not comprise an inhibitor.

The definition of the metallic complexes of formula (I) constituting the catalyst -C-, which is the essential compound of the composition according to the invention, is completed hereinbelow.

The metals of group 8 represented by M in formula (I) are, for example, palladium, platinum or nickel in oxidation state 0. In practice, M represents platinum in oxidation state 0.

The term "alkyl" denotes a linear or branched, saturated hydrocarbon-based chain, which is optionally substituted (e.g. with one or more alkyls), preferably of from 1 to 10 carbon atoms, for example from 1 to 8 carbon atoms and better still from 1 to 7 carbon atoms.

Examples of alkyl groups are especially methyl, ethyl, isopropyl, n-propyl, tert-butyl, isobutyl, n-butyl, n-pentyl, isoamyl and 1,1dimethylpropyl. The alkyl portion of the alkoxy radical is as defined above.

The term "cycloalkyl" means a mono- or polycyclic, preferably mono- or bicyclic, saturated hydrocarbon-based radical preferably containing from 3 to 10 carbon atoms and better still from 3 to 8 carbon atoms. The expression "polycyclic saturated hydrocarbon-based radical" means a radical containing two or more cyclic nuclei linked together via σ bonds and/or fused in pairs. Examples of polycyclic cycloalkyl groups are adamantane and norbornane. Examples of monocyclic cycloalkyl groups are cyclopropyl, cyclobutyl, cyclpentyl, cyclohexyl, cycloheptyl and cyclooctyl.

The term "perfluoroalkyl" denotes an alkyl comprising at least one perfluoroalkyl group, preferably having the formula:

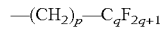

in which p represents 0, 1, 2, 3 or 4; q is an integer from 1 to 10; and $C_qF_{2q+1}$ is linear or branched. Preferred examples of this radical are:

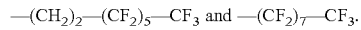

The term "aryl" denotes a monocyclic or polycyclic, and preferably monocyclic or bicyclic, aromatic hydrocarbon-based group containing from 6 to 18 carbon atoms. It should be understood that, in the context of the invention, the term "polycyclic aromatic radical" means a radical containing two or more aromatic nuclei, which are fused (ortho-fused or ortho- and peri-fused) together, i.e. having, in pairs, at least two carbons in common.

Said aromatic hydrocarbon-based group ("aryl") is optionally substituted, for example, with one or more $C_1$–$C_3$ alkyls, one or more halohydrocarbon-based radicals (e.g. $CF_3$), one or more alkoxy (e.g. $CH_3O$) or one or more hydrocarbon-based radicals comprising one or more ketone units (e.g. $CH_3CO$—)

Examples of aryls that may be mentioned include phenyl, naphthyl, anthryl and phenanthryl radicals.

The term "arylalkyl" denotes an alkyl group as defined above, substituted with one or more aryl groups on its hydrocarbon-based chain, the aryl group being as defined above. Examples of these are benzyl and triphenylmethyl.

The term "acyl" means a group R°—CO— in which R° represents alkyl as defined above; or a group Ar—CO— in which Ar represents an aryl group as defined above, or alternatively an arylalkyl group in which aryl and alkyl are as defined above and in which the aryl portion is optionally substituted, e.g. with an alkyl.

The term "alkenyl" means a linear or branched, substituted or unsubstituted, unsaturated hydrocarbon-based chain containing at least one olefinic double bond, and more preferably only one double bond. The alkenyl group preferably contains from 2 to 8 and better still from 2 to 6 carbon atoms. This hydrocarbon-based chain optionally comprises at least one hetero atom such as O, N or S.

Preferred examples of alkenyl groups are allyl and homoallyl groups.

According to the invention, the term "alkynyl" means a linear or branched, substituted or unsubstituted, unsaturated hydrocarbon-based chain containing at least one acetylenic triple bond, and more preferably only one triple bond. The alkynyl group preferably contains from 2 to 8 carbon atoms and better still from 2 to 6 carbon atoms. Examples that may be mentioned include the acetylenyl group and the propargyl group. This hydrocarbon-based chain optionally comprises at least one hetero atom such as O, N or S.

The expression "represents nothing" means that the substituents $-T_3$, or $-T_4$, respectively, are not present. Specifically, in formula (II), the nitrogen atom is trivalent, such that when A or B represents N, the nitrogen atom cannot contain an additional substituent.

Preferably, in the carbene ligands of formula (II):

$T_3$ and $T_4$ represent a hydrogen atom or together form a phenyl, and/or $T_1$ and $T_2$, which may be identical or different, represent $(C_1–C_8)$alkyl or $(C_3–C_8)$cycloalkyl, preferably in the group of radicals comprising: methyl, n-propyl, n-pentyl, neopentyl (—$CH_2$—$C(CH_3)_3$), cyclopentyl, cyclohexyl, adamantyl, allyl (—$CH_2$—$CH$=$CH_2$), methallyl (—$CH_2$—$C(CH_3)$=$CH_2$), propargyl, homopropargyl (—$(CH_2)_2$—$C\equiv CH$), or

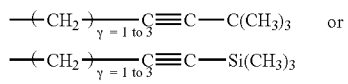

or alternatively: —$(CH_2)_{\gamma=1\ to\ 4}$-amine (for example $N(CH_3)_2$);

or —$(CH_2)_{\gamma=1\ to\ 4}$-alkoxy (for example $O(CH_3)_2$);

and/or A and B both represent a carbon atom.

According to one variant, the carbenes of formula (II) corresponding to the ligand $L_\gamma$ in the catalyst -C- may contain at least two fused nuclei, i.e. at least two substituents from $T_1$, $T_2$, $T_3$ and $T_4$, located on two adjacent ring members, together form a saturated or unsaturated hydrocarbon-based chain preferably containing from 3 to 6 carbon atoms. The expression "saturated or unsaturated hydrocarbon-based chain" means a linear or branched hydrocarbon-based chain possibly containing one or more unsaturations of olefinic double bond type or of acetylenic triple bond type.

When the carbenes (II) contain fused nuclei, they thus correspond to one of the formulae below, in which (alk) represents a saturated or unsaturated hydrocarbon-based chain:

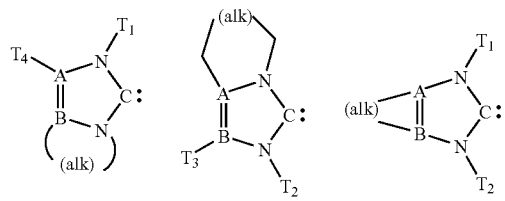

The ligands $L\alpha$ and $L\beta$ of the catalyst -C- of formula (I), belonging to the composition according to the invention, may independently-represent an alkynyl of formula (III.1) or an alkenyl of formula (III.2) substituted with radicals $Z^1$ to $Z^6$ bearing at least one electron-withdrawing unit, which is active toward the π unsaturation of $L\alpha$ and $L\beta$, to promote ligand binding with the metal M of the complex.

Advantageously, in formulae (III.1) and (III.2), the electron-withdrawing residues are chosen from the group comprising:

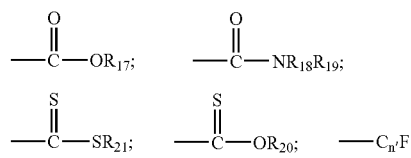

in which:

$R_{17}$, $R_{18}$, $R_{19}$ and $R_{20}$ are a substituted or unsubstituted alkyl, alkenyl, alkynyl or trialkylsilyl, and n' is between 1 and 50.

Examples of radicals $Z^1$ to $Z^6$ that may be mentioned include:

those selected from the group comprising: —CN, —$COOCH_3$, —$COOCH_2CH_3$, —$CONC_{12}H_{25}$, and, in the case where the substituents $Z^1$ and $Z^2$ form, in pairs and with the triple bond, in (III.1), a ring Cy1 and where $Z^3$ to $Z^6$ form in pairs, with or without the double bond, in (III.2), a ring Cy2, these rings Cy1 and Cy2 are independently and preferably chosen from the group comprising the following rings:

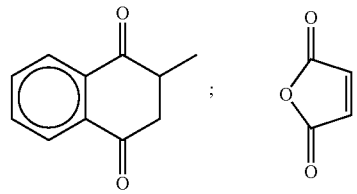

When $L\alpha$ and $L\beta$ together form a ligand $L\delta$ of formula (IV), this ligand is preferably of the type in which $Y_1$ and $Y_2$ either both represent $CR_aR_b$ or both represent $SiR_cR_d$, such that said complexes either have the formula (IV.1) or the formula (IV.2):

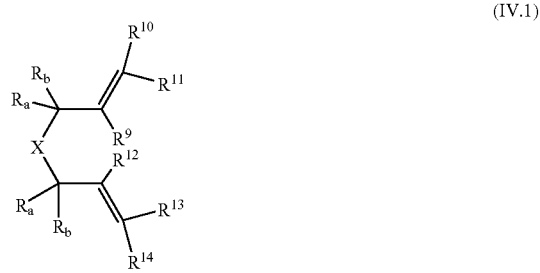

(IV.1)

-continued

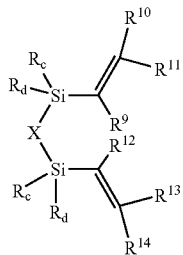
(IV.2)

in which the two $R_a$, the two $R_b$, the two $R_c$ and the two $R_d$ are identical to each other, and $R^9=R^{12}$; $R^{10}=R^{14}$; and $R^{11}=R^{13}$.

According to one variant, the two $R_c$ in (IV.2) together form:

(a) either a chain

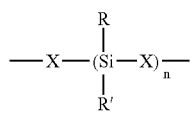

in which n is an integer from 1 to 3; X is as defined above; and R and R', which may be identical or different, take any of the meanings given above for $R_d$, it being understood that, when n is 2 or 3, only one silicon atom of said chain may be substituted with one or two alkenyl or alkynyl groups;

(b) or a saturated hydrocarbon-based chain, such that the two substituents $R_c$, together with the two silicon atoms that bear them and X, form a 6- to 10-membered and preferably a 6- to 8-membered ring.

When the two $R_c$ form the chain (a) in (IV.2), it is preferable for n to be 1 or 2 (and better still n is 1) and for $R=R_d$, the two groups $R_d$ borne by the two silicon atoms being identical. In this case, $R_d$ preferably represents alkyl, for example methyl. Better still, in these compounds, R' represents $—CR_{12}=CR_{13}R_{14}$; $R_{13}=R_{11}$; $R_{10}=R_{14}$; and $R_{12}=R_9$.

In this case, it is preferable for X to represent O in (IV.2). The ligand Lδ then has the formula:

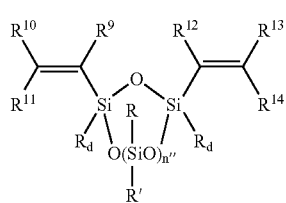
(IV.2.2)

Among these compounds, it is preferable for the two $R_d$ to be identical and advantageously to represent alkyl (for example methyl).

Preferably, n is 1 or 2 and $R=R_d$, it being understood that when n is 2, only one silicon atom of the chain $O—(SiRR'—O)_n—$ may be substituted with one or two alkenyl or alkynyl groups. Better still, $R'=—CR_{12}=CR_{13}R_{14}$ and $R_{13}=R_{11}$; $R_{10}=R_{14}$; and $R_{12}=R_9$.

When the two $R_c$ form, together with the two silicon atoms and the group X, the chain (b), it is preferable for the two groups $R_c$ to be an 8-membered ring. In this case, it is preferable for the two $R_d$ to be identical. The ligand Lδ then has the formula:

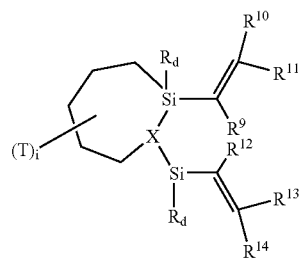
(IV.2.3)

in which T represents alkyl, i is an integer between 0 and 5, T being located on one or more of the ring members 1, 2, 3, 4 and 5 of the above formula.

Similarly, when $Y_1$ and $Y_2$ represent $CR_aR_b$ in (IV.1), the two groups $R_a$ linked to different carbon atoms can together form a saturated hydrocarbon-based chain (c), such that the two groups $R_a$, together with the carbons that bear them and X, form a 6- to 10-membered ring. Preferably, the ring formed is an 8-membered ring, in which case the ligand Lδ then has the formula:

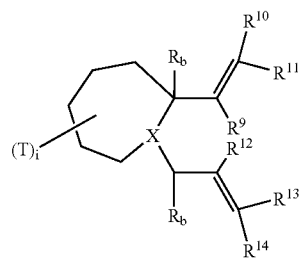
(IV.1.1)

in which T represents alkyl; i is an integer between 0 and 5, T being located on one or more of the ring members 1, 2, 3, 4 and 5 of the above formula.

When $R_f$ and/or $R_g$ represents $SiG_1G_2G_3$, it is preferable for $R_f$ and/or $R_g$ to be trialkylsilyl, for example $SiG_1G_2G_3$ in which $G_1=G_2=G_3=$alkyl.

Subgroups of the ligands Lδ of the metallic complexes (catalyst -C-) that form part of the composition according to the invention consist of the complexes for which:

X=O; $Y_1$ and $Y_2$ independently represent $SiR_cR_d$; or

X=$NR_e$; $Y_1$ and $Y_2$ independently represent $CR_aR_b$; or

X=$NR_e$; $Y_1$ and $Y_2$ independently represent $SiR_cR_d$; or

X=$CR_fR_g$; $Y_1$ and $Y_2$ independently represent $CR_aR_b$; or

X=$CR_fR_g$; $Y_1$ and $Y_2$ independently represent $SiR_cR_d$.

Among these ligands Lδ of formula (IV), the ones that are preferred are those for which:

when X represents O, $Y_1$ and $Y_2$ independently represent $SiR_cR_d$; or when X represents $NR_e$, $Y_1$ and $Y_2$ independently represent $CR_aR_b$; or when X represents $CR_fR_g$, $Y_1$ and $Y_2$ independently represent $CR_aR_b$.

In practice, X represents O and $Y_1$ and $Y_2$ independently represent $SiR_cR_d$ in the ligand $L\delta$ of formula (IV).

In the context of the invention, the expression "independently represent" means that the designated substituents are either identical or different.

For example, $R_{10}$, $R_{11}$, $R_{13}$ and $R_{14}$ are hydrogen atoms in the ligands $L\delta$ of formula (IV).

Preferred meanings of $R_9$ and $R_{12}$ are especially a hydrogen atom; an alkyl group; an aryl group optionally substituted with alkyl; and a cycloalkyl group optionally substituted with alkyl. Among these preferred meanings, it is particularly advantageous for $R_9$ and $R_{12}$ which are identical, to represent a hydrogen atom; $(C_3-C_8)$cycloalkyl or $(C_1-C_8)$alkyl.

For example, the diolefinic ligand $L\delta$ of formula (IV) is symmetrical, i.e. $R_{10}=R_{14}$; $R_{11}=R_{13}$; $R_9=R_{12}$ and the two groups $Y_1$ and $Y_2$ are either strictly identical to each other, or $Y_1=CR_aR_b$ and $Y_2=CR_aR_b$ in which the two $R_a$ together form a symmetrical chain, or alternatively $Y_1=SiR_cR_d$ and $Y_2=SiR_cR_d$ in which the two $R_c$ together form a symmetrical chain.

As regards the catalyst -C- of the composition according to the invention, a first particularly preferred group of metallic complexes of formula (I.1) below should be mentioned:

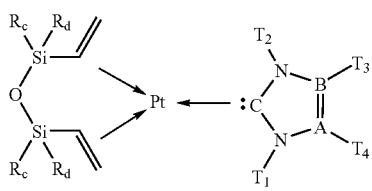

(I.1)

in which:

$T_1$ and $T_2$ are identical and are as defined above;
$T_3$ and $T_4$ are as defined above;
$R_c$ and $R_d$ are as defined above.

A second particularly preferred group of catalysts -C- of the composition according to the invention comprises the metallic complexes of formula (I.2) below:

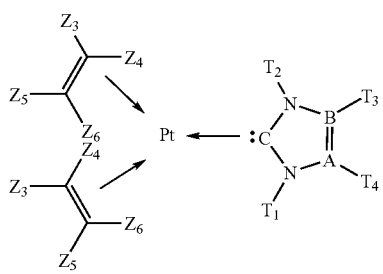

(I.2)

in which:

$T_1$ and $T_2$ are identical and are as defined above;
$T_3$ and $T_4$ are as defined above;
$R_c$ and $R_d$ are as defined above.

A third particularly preferred group of catalysts -C- of the composition according to the invention comprises the metallic complexes of formula (I.3) below:

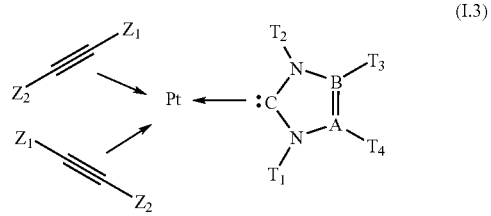

(I.3)

in which:

$T_1$ and $T_2$ are identical and are as defined above;
$T_3$ and $T_4$ are as defined above;
$R_c$ and $R_d$ are as defined above.

Besides the catalyst -C-, the composition according to the invention comprises the two polyaddition-reactive polyorganosiloxane species, namely the POS -A- and the POS -B-. These species are chosen from POSs consisting of siloxyl units of general formula:

$$(R^{20})_xSiO_{4-x/2} \quad (I')$$

and/or of siloxyl units of formula:

$$(R^{21})_y(R^{22})_zSiO_{4-y-z/2} \quad (II')$$

in which formulae the various symbols have the following meaning:

the symbols $R^{20}$ and $R^{22}$, which may be identical or different, each represent a group of nonhydrolyzable hydrocarbon-based nature, this radical possibly being:

an alkyl or haloalkyl radical containing from 1 to 5 carbon atoms and comprising from 1 to 6 chlorine and/or fluorine atoms, cycloalkyl and halocycloalkyl radicals containing from 3 to 8 carbon atoms and from 1 to 4 chlorine and/or fluorine atoms, aryl, alkylaryl and haloaryl radicals containing from 6 to 8 carbon atoms and from 1 to 4 chlorine and/or fluorine atoms, cyanoalkyl radicals containing 3 or 4 carbon atoms;

the symbols $R^{21}$, which may be identical or different, each represent a hydrogen atom, a $C_2-C_6$ alkenyl group, a hydroxyl group, a hydrolyzable atom or a hydrolyzable group;

x=an integer equal to 0, 1, 2 or 3;

y=an integer equal to 0, 1, 2 or 3;

z=an integer equal to 0, 1 or 2;

the sum y+z is between 1 and 3;

with the condition that the POS -A- Si-alkenyl comprises at least one unit $R^{21}$=alkenyl per molecule and the POS -B- Si—H comprises at least one unit $R^{21}$=hydrogen per molecule;

preferably $R^{20}$=methyl; ethyl; propyl; isopropyl; butyl; isobutyl; n-pentyl; t-butyl; chloromethyl; dichloromethyl; α-chloroethyl; α,β-dichloroethyl; fluoromethyl; difluoromethyl; α,β-difluoroethyl; 3,3,3-trifluoropropyl; trifluorocyclopropyl;

4,4,4-trifluorobutyl; 3,3,4,4,5,5-hexafluoropentyl; β-cyanoethyl; γ-cyanopropyl; phenyl; p-chlorophenyl; m-chlorophenyl; 3,5-dichlorophenyl; trichlorophenyl; tetrachlorophenyl; o-, p- or m-tolyl; α,α,α-trifluorotolyl; xylyls such as 2,3-dimethylphenyl, 3,4-dimethylphenyl and even more preferably methyl or phenyl, these radicals possibly being optionally halogenated or alternatively cyanoalkyl radicals;

$R^{21}$=hydrogen or vinyl.

These POSs -A- and -B- are, for example, respectively, a polyorganovinylsiloxane and a polyorganohydrogenosiloxane. The various organic substituents of the vinyl reactive groups and of the hydrogen are, for example, methyls or cyclohexyls. The hydrogens and vinyls are borne by siloxyl units M=[$R_3SiO$—] and/or D=[—$(R)_2SiO$—] and/or T=[—(R)SiO—]. These hydrogenated or vinyl-containing units M and D each comprise one or more H or vinyl, preferably only one.

The number of SiH or SiVi units per molecule is greater than or equal to 1, preferably at least equal to 10 and better still between 10 and 100.

This can represent from 0.01% to 10% (preferably 0.1% to 2%) of vinyl by weight for the POS -A- and from 0.001% to 5% (preferably 0.05% to 2%) of hydrogen by weight for the POS -B-.

Polymers that are suitable are polymethylhydrogenosiloxanes containing —$Si(CH_3)_3$ end groups and polydimethylsiloxanes containing —$Si(CH_3)_2H$ end groups, methylhydrogenodimethylsiloxane copolymers containing —$Si(CH_3)_2H$ end groups, methylhydrogenomethyloctylsiloxane copolymers and methylhydrogenocyclosiloxane polymers.

In general, the POSs -A- and -B- that may be used in the reaction have an average molecular mass of between $1 \times 10^2$ and $1 \times 10^6$ (g/mol).

For the POS -A-, this especially encompasses, in terms of dynamic viscosity at 25° C., ranges:
of POSs that are polyaddition-vulcanizable at elevated temperature (EVC), with a viscosity at least equal to $1 \times 10^5$ mPa.s, preferably between $1 \times 10^6$ and $1 \times 10^7$ mPa.s, and even better, for the
and POSs that are polyaddition-vulcanizable at elevated temperature of the liquid silicone elastomer (LSR) type, with a viscosity preferably of between $1 \times 10^5$ and $5 \times 10^5$ mPa.s.

According to one preferred mode of the invention, the silicone compositions concerned are POSs that are polyaddition-vulcanizable at elevated temperature (EVC) in which the POSs -A- may in practice have a viscosity at 25° C. of, for example, $2 \times 10^6$ mPa.s, and the POSs -B- from 10 to 5000 mPa.s (for example 300 mPa.s).

In these examples, the viscosity is measured using a Brookfield viscometer according to the indications of AFNOR standard NFT 76 106 of May 1982.

All the viscosities considered in the present description correspond to a "Newtonian" dynamic viscosity magnitude at 25° C., i.e. the dynamic viscosity that is measured, in a manner that is known per se, at a shear rate gradient low enough for the measured viscosity to be independent of the rate gradient.

The composition according to the invention may also contain a certain number of standard ingredients, besides the POSs -A- and -B- and the catalyst -C-, including, especially, at least one crosslinking inhibitor -B- capable of stopping the polyaddition reaction and of allowing the conservation of the one-component composition ABCD, in a not fully crosslinked state.

Thus, the invention relates to silicone compositions comprising at least one inhibitor -D- in which the catalyst -C- is chosen from the metal complexes
of formula (I.1) below:

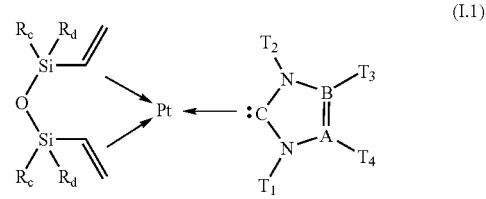

(I.1)

of formula (I.2) below:

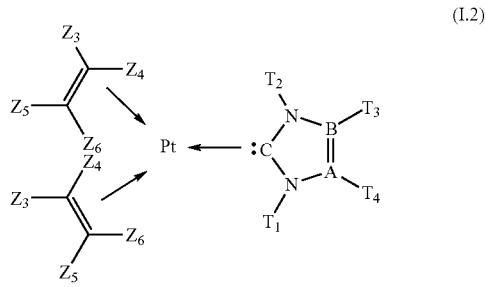

(I.2)

in which:

$T_1$ and $T_2$ are identical and are as defined above;

$T_3$ and $T_4$ are as defined above;

$R_c$ and $R_d$ are as defined above;

$Z^1$ to $Z^6$ are free of electron-withdrawing radical(s);

and/or of formula (I.3) below:

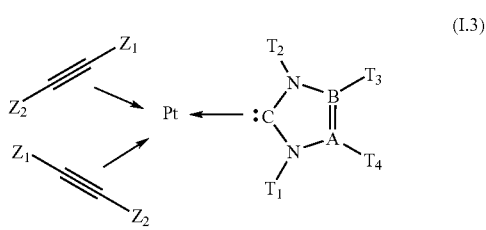

(I.3)

in which:

$T_1$ and $T_2$ are identical and are as defined above;

$T_3$ and $T_4$ are as defined above;

$R_c$ and $R_d$ are as defined above;

$Z^1$ and $Z^2$ are free of electron-withdrawing residue(s).

These compositions have long pot lives.

It should be noted that, for certain catalysts -C-, especially those comprising a carbene (II) and at least one (and preferably two) ligands Lα and Lβ of formula (III.1) or (III.2), it is not necessary to use an inhibitor.

Thus, the invention is also directed toward silicone compositions free of inhibitor -D-, in which the catalyst -C- is chosen from the metallic complexes:
of formula (I.2) below:

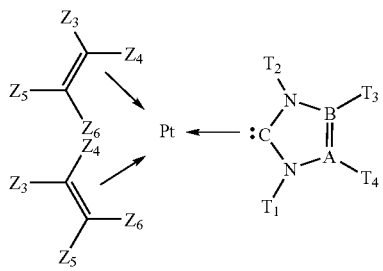

(I.2)

in which:
$T_1$ and $T_2$ are identical and are as defined above;
$T_3$ and $T_4$ are as defined above;
$R_c$ and $R_d$ are as defined above;
at least one of the substituents $Z^1$ to $Z^6$ (preferably each substituent) comprises at least one electron-withdrawing residue;
and/or of formula (I.3) below:

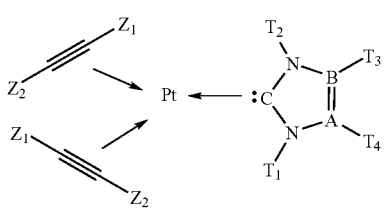

(I.3)

in which:
$T_1$ and $T_2$ are identical and are as defined above;
$T_3$ and $T_4$ are as defined above;
$R_c$ and $R_d$ are as defined above;
$Z^1$ and $Z^2$ are free of electron-withdrawing residue(s).

These inhibitor-free compositions are endowed—entirely advantageously and unexpectedly—with long pot lives in an ambient atmosphere. The crosslinking takes place only at elevated-temperature. This advantage is economically fundamental and fundamental in terms of the ease of use and of storage.

Advantageously, the inhibitors -D- (if used) are selected from:
polyorganosiloxanes, which are advantageously cyclic, substituted with at least one alkenyl, tetramethylvinyltetrasiloxane being particularly preferred,
unsaturated amides,
alkyl, alkenyl or alkynyl maleates, diallyl maleate being particularly preferred,
acetylenic alcohols,
alkyl, alkenyl or alkynyl acetylenedicarboxylates,
and combinations thereof.

As regards the acetylenic alcohols (cf. FR-B-1 528 464 and FR-A-2 372 874), it may be mentioned that they form part of the preferred hydrosilylation-reaction thermal blockers, and they have the formula:

in which formula:
$R^x$ is a linear or branched alkyl radical, or a phenyl radical;
$R^y$ is H or a linear or branched alkyl radical, or a phenyl radical;
the radicals $R_x$, $R^y$ and the carbon atom located α to the triple bond possibly forming a ring;
the total number of carbon atoms contained in $R^x$ and $R_y$ being at least 5 and preferably from 9 to 20.

Said alcohols are preferably chosen from those with a boiling point of greater than 250° C. Examples that may be mentioned include:
1-ethynyl-1-cyclohexanol;
3-methyl-1-dodecyn-3-ol;
3,7,11-trimethyl-1-dodecyn-3-ol;
1,1-diphenyl-2-propyn-1-ol;
3-ethyl-6-ethyl-1-nonyn-3-ol;
3-methyl-1-pentadecyn-3-ol.

These α-acetylenic alcohols are commercial products.
Such a retardant (D) is present in a proportion of not more than 3000 ppm and preferably in a proportion of from 100 to 2000 ppm relative to the total weight of the organopolysiloxanes (A) and (B).

As common families of common functional additives that may be used in the silicone compositions according to the invention, mention may be made of:
fillers,
hydroxylated POS oils that are useful as compatibilizers,
adhesion promoters,
adhesion modulators,
pigments,
heat-resistant, oil-resistant or flame-resistant additives (for example metal oxides),
etc.

The fillers that may be envisaged are preferably mineral. They may consist of products chosen from siliceous (or nonsiliceous) materials.

As regards the siliceous materials, they may act as reinforcing or semireinforcing filler.

The reinforcing siliceous fillers are chosen from colloidal silicas, combustion silica powders and precipitation silica powders, or a mixture thereof.

These powders have a mean particle size generally of less than 0.1 μm and a BET specific surface area of greater than 50 m²/g, preferably between 150 and 350 m²/g.

Semireinforcing siliceous fillers such as diatomaceous earths or ground quartz may also be used.

As regards the nonsiliceous mineral materials, they may intervene as semireinforcing mineral filler or as packing mineral filler.

Examples of these nonsiliceous fillers that may be used, alone or as a mixture, include carbon black, titanium dioxide, aluminum oxide, hydrated alumina, expanded vermiculite, nonexpanded vermiculite, calcium carbonate, zinc oxide, mica, talc, iron oxide, barium sulfate and slaked lime.

These fillers have a particle size generally of between 0.001 and 300 μm and a BET surface area of less than 100 m²/g.

In practical but nonlimiting terms, the fillers used may be a mixture of quartz and silica.

The fillers may be treated with any suitable product.

In terms of weight, it is preferred to use an amount of filler of between 20% and 50% and preferably between 25% and 35% by weight relative to the constituents of the composition as a whole.

More generally, in quantitative terms, the compositions according to the invention amount to proportions that are standard in the technical field under consideration, given that the intended application must also be taken into account.

According to another of its aspects, the present invention concerns, as novel products, complexes of formula (I), which are useful especially as catalysts -C- and in which the carbene of formula (II) is such that:

$T_3$ and $T_4$ can form, together with A and B when these each represent a carbon atom, an aryl as defined above, preferably a phenyl;

and/or $T_1$ and $T_2$ independently represent a monovalent radical of formula (V) below:

$$-V_1-V_2 \quad (V)$$

in which:

$V_1$ is a divalent-hydrocarbon-based radical, preferably an optionally substituted linear or branched $C_1$–$C_{10}$ alkylene, $V_2$ is a monovalent radical chosen from the following group of substituents:

alkoxy, —$OR^v$ with $R^v$ corresponding to hydrogen, alkyl or aryl amine, preferably $N(R^v)_2$ with $R^v$ corresponding to hydrogen, alkyl or aryl or alternatively $T_1$ and $T_2$ independently represent a monovalent radical of formula (W) below:

$$-W_1-\omega-W_2 \quad (W)$$

in which:

$W_1$ is a divalent hydrocarbon-based radical, preferably an optionally substituted linear or branched $C_1$–$C_{10}$ alkylene, ω represents:

—$R^\alpha C=CR^\alpha$— with $R^\alpha$ corresponding to H or alkyl or

—C≡C—

$W_2$ is a monovalent radical chosen from the following group of substituents:

$R^\beta$=alkyl or H;

Si-alkyl, Si-alkenyl or Si-alkynyl, preferably —Si(alkyl)$_3$;

alcohol, preferably —$C(R^\epsilon)_2OH$ with $R^\epsilon$=H or alkyl;

ketone, preferably

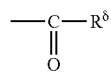

with $R_\delta$=alkyl; alkenyl, alkynyl;
carboxyl, preferably

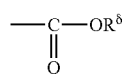

with $R_\delta$=alkyl; alkenyl, alkynyl;
amide, preferably

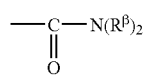

with $R^\beta$=H, alkyl; alkenyl, alkynyl;
acyl, preferably

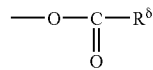

with $R^\delta$=alkyl; alkenyl, alkynyl;

$T_1$ and $T_2$ preferably independently corresponding to a radical W of the type

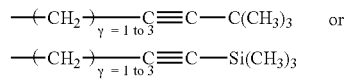

or alternatively to one of the following units: methyl, isopropyl, tert-butyl, n-pentyl, neopentyl, cyclopentyl, cyclohexyl, adamantyl, allyl, methallyl, propargyl or homopropargyl, or alternatively the substituents $T_1$, $T_2$, $T_3$ and $T_4$ can form in pairs, when they are located on two adjacent ring members in formula (II), a saturated or unsaturated hydrocarbon-based chain.

A subject of the invention is also other novel metallic complexes of formula (I) in which:

Lγ is as defined above,

Lα and Lβ correspond independently to the compounds of formula (II), (III.1) or (III.2) as defined above.

Examples of these novel catalysts that may be mentioned include:

those of formula (I.2) below:

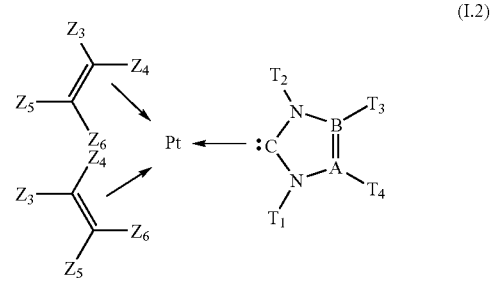

in which:

$T_1$ and $T_2$ are identical and are as defined above;

$T_3$ and $T_4$ are as defined above;

$R_c$ and $R_d$ are as defined above;

or those of formula (I.3) below:

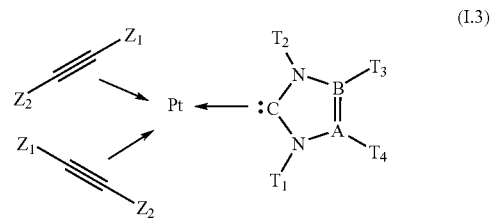

in which:

$T_1$ and $T_2$ are identical and are as defined above;

$T_3$ and $T_4$ are as defined above;

$R_c$ and $R_d$ are as defined above.

It should be noted that, in these formulae (I.1), (I.2) and also (I.3), the platinum may be replaced with any metal M as defined above.

The invention also covers any catalytic composition comprising, as active material, one or more metallic complexes (I) as defined above and comprising at least one ligand Lα or Lβ (better still two ligands) of formula (III.1) or (III.2).

Such catalysts (especially hydrosilylation catalysts) have the particular feature of being able to be formed in situ, in silicone compositions of the type according to the invention, provided that they comprise ligands Lα and Lβ, of formula (III.1) or (III.2), for example as inhibitor -D-. This or these ligands Lα and Lβ, of formula (III.1) or (III.2) are capable of displacing the initial ligands Lδ of the catalyst -C-. Such catalysts are latent catalysts. The present invention obviously covers this case.

Another subject of the invention consists of a process for the hydrosilylation of olefins or of acetylenic derivatives (for example hydrosilylation of one or more POSs -A- using one or more POSs -B-), characterized in that it consists in using the silicone composition as defined above and/or the catalytic composition also described above.

According to one advantageous variant in which at least one latent catalyst as described above is used, use is made of a silicone composition according to the invention, as presented above and comprising at least one inhibitor -D- allowing the in situ formation of at least one metallic complex comprising at least one ligand Lα or Lβ, of formula (III.1) or (III.2).

Surprisingly, when the hydrosilylation is performed using as catalysts the metallic complexes prepared by the process according to the invention, formation of these side products is greatly limited. More particularly, a strong reduction in the level of isomers formed, and also a faint coloration, resulting from the decomposition of the catalyst, are observed.

The hydrosilylation reaction may be performed in a solvent or in the absence of solvent. As a variant, one of the reagents may act as solvent: for example, the compound containing an ethylenic double bond or containing an acetylenic triple bond.

Suitable solvents are solvents that are miscible with the compound containing an Si—H unit.

Under the conditions of the hydrosilylation reaction, the catalytic complex should be dissolved in the reaction medium.

Examples of solvents that may be used for the hydrosilylation are especially aliphatic hydrocarbons (such as pentane, hexane, heptane, pentamethylheptane or petroleum distillation fractions); aromatic hydrocarbons (such as benzene, toluene and xylenes: ortho-xylene, para-xylene and meta-xylene); halogenated aliphatic or aromatic hydrocarbons (such as tetrachloroethylene); or ethers (such as tetrahydrofuran or dioxane).

The hydrosilylation reaction may be performed at a temperature of between 15° C. and 300° C., for example between 20 and 240° C., better still between 70 and 200° C., especially between 50 and 150° C. and very preferably between 100 and 100° C.

The relative amount of unsaturated compound and of compound containing an Si—H unit may be controlled so as to ensure reaction of all the unsaturations with Si—H bonds.

Generally, the molar ratio of the unsaturations to the Si—H bonds ranges between 1:100 and 10:1.

According to the invention, the hydrosilylation reaction is performed in the presence of a catalytic amount of one or more complexes according to the invention. The term "catalytic amount" means less than one molar equivalent of platinum relative to the amount of unsaturations present in the reaction medium.

In general, it suffices to introduce into the reaction medium less than 1000 ppm, preferably less than 100 ppm and better still less than 50 ppm of platinum, calculated relative to the total mass of the unsaturated compound and of the compound containing Si—H units.

As regards the preparation of the composition according to the invention, it is a matter of using and mixing together the compounds -A-, -B-, -C-, optionally -D- and one or more other conventional additives.

The mixing operations are entirely within the capability of the person skilled in the art.

The POSs -A- and -B-, the inhibitors -D- and the other standard additives, such as fillers, are commodities that are entirely available or accessible to those skilled in the art.

As regards the metallic complexes (I) forming the catalysts -C-, it has been seen above that the catalysts -C- comprising complexes:

(I)

with Lα and/or Lβ, of formula (III.1) or (III.2), may be obtained from complexes (I) in which Lγ is of formula (II) and Lα and Lβ are of formula (IV), these ligands being displaced in situ with inhibitors -D- of formula (III.1) or (III.2).

These complexes (I) in which Lγ is of formula (II) and Lα and Lβ are of formula (IV) are conventionally prepared, for example from complexes known in the prior art by ligand exchange, i.e. by addition of the appropriate carbene of formula II to a metallic complex of the metal M, in solution, referred to as the precursor complex.

Examples of suitable precursor complexes include the Karstedt complex of formula:

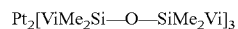

in which Vi represents a vinyl radical.

The complexes of formula I are generally prepared from precursor complexes containing, as ligand, at least one diolefinic compound of formula (IV.P):

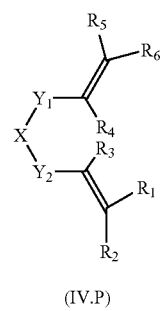

(IV.P)

III in which $R_1$, $R_2$, $R_3$, $R_4$, $R_5$, $R_6$, X, $Y_1$ and $Y_2$ are as defined above for formula I.

These ligands are either commercially available or are easily prepared by a person skilled in the art from commercial compounds.

When X represents $NR_e$ and $Y_1$ and $Y_2$, independently of each other, represent $CR_aR_b$, the compounds of formula (IV.P) have amines that are easily prepared by performing standard processes of organic chemistry. Thus, when $R_e$ is different than a hydrogen atom, these amines may be readily prepared from the corresponding primary amine of formula $R_eNH_2$ via the action of suitable chlorides, preferably in the presence of an organic or mineral base.

When the diolefin (IV.P) is symmetrical (i.e. $R_4=R_3$; $R_5=R_2$; $R_1=R_6$; and $Y_1=Y_2$), $R_eNH_2$ is reacted with two equivalents of a chloride of formula:

$$Cl—CR_aR_b—CR_3=CR_1R_2 \quad (IV.P')$$

in the presence of a base.

When the diolefin (IV.P) is dissymmetrical, it is preferable to protect the amino group of $R_eNH_2$ with a suitable conventional protecting group P before reacting the resulting compound of formula $R_eNHP$ with a chloride of formula (IV.P''):

$$Cl—CR_aR_b—CR_3=CR_1R_2 \quad (IV.P'')$$

in the presence of a suitable base.

Next, after deprotection, the resulting amine is reacted with a chloride of formula (IV.P'''):

$$Cl—CR_aR_b—CR_4=CR_5R_6 \quad (IV.P''')$$

so as to obtain the expected amine.

In formulae IV.P', IV.P'' and IV.P''' above, the substituents $R_1, R_2, R_3, R_4, R_5$ and $R_6$ are as defined for formula I; $R_a$ and $R_b$ are as defined above.

The protecting groups P for the amine functions and the corresponding deprotection methods are described in Protective Groups in Organic Synthesis, Greene T. W. and Wuts P. G. M., published by John Wiley & Sons, 1991, and in Protecting Groups, Kocienski P. J., 1994, Georg Thieme Verlag.

When $R_e$ represents a hydrogen atom, it is desirable to select, as starting compound, the amine of formula IV.Q below, protected beforehand on the amino function with a protecting group P as defined above:

$$NH_2—CR_a^2R_b^2—CR_3=CR_1R_2 \quad (IV.Q).$$

The protected amine IV.Q is reacted with a chloride of formula VI as defined above, preferably in the presence of a base, and, after deprotection of the amino function, to give the expected compound of formula IV.P is isolated.

Examples of suitable bases include an organic base chosen from triethylamine, diisopropylamine, pyridine and N,N-dimethylaniline or a mineral base such as NaOH, KOH, NaHCO$_3$, Na$_2$CO$_3$, KHCO$_3$ and K$_2$CO$_3$.

When X represents O and Y represents $CR_aR_b$, the compounds of formula (IV) are ethers. These ethers are commercially available or prepared in a manner that is known per se from commercially available compounds.

The compounds of formula IV in which X represents $CR_fR_g$ and Y represents $CR_aR_b$ are diolefins that are readily available to those skilled in the art by synthesis or are commercially available.

The compounds of formula IV in which X represents $NR_e$ in which $R_e$ represents H or alkyl; $R_1=R_6$; $R_2=R_5$; $R_3=R_4$; and $Y_1=Y_2=SiR_cR_d$, may be prepared via the action of an amine $R_e—NH_2$ with two equivalents of a silyl chloride of formula:

$$ClSiR_cR_d—CR_3=CR_1R_2$$

in which $R_c$, $R_d$, $R_1$, $R_2$ and $R_3$ are as defined above.

The compounds of formula IV in which X represents $NR_e$, $R_e$ being as defined above in formula I; $Y_1=Y_2=SiR_cR_d$ in which $R_d$ is as defined above in formula I; the two groups $R_c$ together form the chain:

$$—NR_a—(SiR_aR_c°—NR_a)_n—$$

in which $R_a$ and $R_d$ are as defined above; n represents an integer from 1 to 3; $R_d°$ represents —$CR_3=CR_1R_2$; $R_1=R_6$; $R_2=R_5$ and $R_3=R_4$, may be prepared by reacting the amine $R_e—NH_2$ with the silyl chloride of formula:

$$Cl_2SiR_d—CR_3=CR_1R_2$$

in which $R_d$, $R_1$, $R_2$ and $R_3$ are as defined above.

The compounds of formula IV in which X represents O and $Y_1$ and $Y_2$ represent $SiR_cR_d$ are linear, branched or cyclic siloxanes that are commercially available or that may be prepared from commercial compounds, by performing standard processes of the prior art. Examples of preferred siloxanes of formula IV are ViMe$_2$SiOSiMe$_2$Vi and (MeViSiO)$_3$, the second formula representing a cyclosiloxane in which Vi represents vinyl.

In the case of the symmetrical compounds of formula IV, i.e. those in which $R_1=R_6$; $R_2=R_5$; $R_3=R_4$ and $Y_1=Y_2$, one of the following synthetic variants may be performed.

(Variant a): For the preparation of said symmetrical siloxanes of formula IV for which $R_1, R_2, R_3, R_c$ and $R_d$ are independently chosen from alkyl, aryl, alkenyl and alkynyl, a silyl chloride of formula Cl$_2$SiR$_c$R$_d$ may be reacted with an organometallic compound of formula:

$$CR_1R_2=CR_3—Mg-Hal$$

in which $R_1$, $R_2$ and $R_3$ are as defined above and hal represents a halogen atom, under the usual reaction conditions using magnesium reagents.

(Variant b): For the preparation of said symmetrical siloxanes of formula IV for which $R_1=R_2=R_3=H$ and $R_c$ and $R_d$ are chosen from alkenyl, alkynyl, aryl and alkyl, a silyl chloride of formula Cl$_2$SiR$_c$—CH=CH$_2$ may be-reacted with an organometallic compound of formula:

$$R_d—Mg-hal$$

in which $R_d$ is as defined above and hal represents halogen.

A person skilled in the art may refer to J. Gen. Chem., USSR, 1977, 47, 1402–1406 to perform this variant.

(Variant c): For the preparation of said symmetrical siloxanes of formula IV in which $R_1=R_3=H$ and $R_2$ represents alkyl, a siloxane of formula:

$$H—SiR_cR_d—O—SiR_cR_dH$$

may be reacted with two equivalents of an acetylenic hydrocarbon of formula H—C≡C—R$_2$ in which $R_2$ is as defined above.

Cyclic siloxanes of formula IV are described in U.S. Pat. No. 4,593,084.

The compounds of formula IV in which X represents $CR_fR_g$ and $Y_1$ and $Y_2$ independently represent —$SiR_cR_d$ may be prepared by performing a process analogous to one of those described in:

J. of Organometallic Chemistry, 1996, Vol. 521, 99–107 (this process being particularly suitable for preparing the symmetrical compounds of formula IV in which $Y_1=Y_2$; $R_f=R_g=H$; $R_c$ and $R_d$ represent alkyl or aryl optionally substituted with alkyl; $R_3$ represents a hydrogen atom; alkyl; or optionally substituted aryl; and $R_1$ and $R_2$ are chosen from a hydrogen atom and alkyl);

J. of Organometallic Chemistry, 1997, Vol. 545–546, 185–189 (this process being particularly suitable for preparing symmetrical compounds of formula IV in which $Y_1=Y_2$; $R_f=R_g=Cl$ or Br; $R_c$ and $R_d$ represent alkyl; $R_1=R_2=R_3=$a hydrogen atom);

J. Chem. Soc., Perkin Trans II, 1987, p. 381 (this process being more particularly suitable for preparing the symmetrical compounds of formula III in which $Y_1=Y_2$; $R_f=R_g=SiG_1G_2G_3$; $R_c$ and $R_d$ represent alkyl; $R_1=R_2=R_3=$a hydrogen atom).

The carbenes of formula II may be prepared by deprotonation of imidazolium salts, tetrazolium salts, triazolium salts or pyrazolium salts, depending on the case, under the action of a base.

These reactions may be represented schematically as follows:

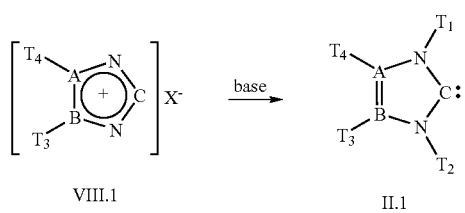

VIII.1    II.1

In these reaction schemes, $T_1$, $T_2$, $T_3$, $T_4$, A and B are as defined above for formula I and $X^-$ represents an anion.

The nature of the anion $X^-$ is not critical according to the invention. The anion $X^-$ is the anion derived from a mineral or organic Brönsted acid (protic acid). Usually, the anion $X^-$ is derived from an acid with a pKa of less than 6. Preferably, $X^-$ is derived from an acid with a pKa of less than 4 and better still less than 2. The pKa values that are involved herein are the pKa values of the acids as measured in water.

Examples of acids are the carboxylic acids of formula $G_o$—COOH in which $G_o$ represents alkyl, for example $(C_1–C_{22})$alkyl; or aryl, for example $(C_6–C_{18})$aryl optionally substituted with one or more alkyl, preferably one or more $(C_1–C_6)$alkyl; the sulfonic acids of formula $G_oSO_3H$ in which $G_o$ is as defined above; and the phosphonic acids of formula $G_oPO_3H$ in which $G_o$ is as defined above; other acids are HF, HCl, HBr, HI, $H_2SO_4$, $H_3PO_4$ and $HClO_4$.

Preferred examples of carboxylic acids are acetic acid, benzoic acid and stearic acid. A preferred sulfonic acid that will be mentioned is benzenesulfonic acid, and a preferred phosphonic acid that will be mentioned is phenylphosphonic acid.

According to the invention, the anions $X^-$ derived from acids HF, HCl, HBr, HI, $H_2SO_4$, $HBF_4$ and $H_3PO_4$ are more particularly preferred.

Thus, anions $X^-$ that are particularly preferred according to the invention are halide, sulfate, hydrogen sulfate, phosphate, hydrogen phosphate and dihydrogen phosphate anions. Anions that may also be mentioned include tetrafluoroborates and hexaphenylphosphate.

The bases that may be used for the deprotonation of the salts of formula VIII are strong bases chosen from alkali metal hydrides, alkali metal hydroxides, alkali metal carboxylates, alkali metal alkoxides and alkali metal amides.

Examples of suitable bases are thus sodium hydride, sodium methoxide, potassium tert-butoxide and lithium diisopropylamide, and mixtures thereof.

The deprotonation reaction is preferably performed in a solvent capable of at least partially dissolving the starting salt of formula VIII and also the other reagents.

The nature of the solvent also depends on the strength of the base. Specifically, in the case of a strong base and of particularly reactive starting salts, it may be necessary to perform the process at low temperature.

Generally, the reaction temperature is between 40 and −78° C., preferably between 30 and −50° C. and better still between 25 and −40° C., for example between 20 and −30° C.

Solvents that may be used in the carbene preparation process are cyclic or noncyclic ethers, such as diethyl ether, diisopropyl ether, tetrahydrofuran, dioxane, dimethoxyethane or diethylene glycol dimethyl ether.

Other solvents that may be used are dimethyl sulfoxide, dimethylformamide, dimethylacetamide, hexamethylphosphorylamide: $[(CH_3)_2N]_3PO$ and hexamethylphosphoramide $[(CH_3)_2N]_3P$.

The carbenes of formula II in which A and B both represent a carbon atom may also be prepared by reducing the corresponding thiones of formula IX:

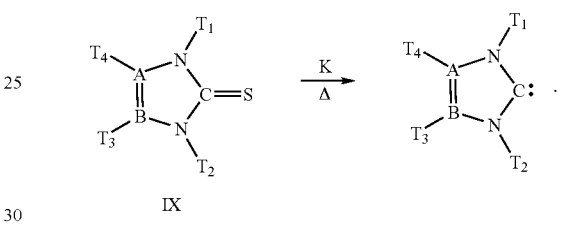

IX

This reaction was described by N. Kuhn in Synthesis, 1993, 561. Preferably, the reaction is performed in a solvent of the ether or amide type, as defined above, at a temperature of between 50 and 150° C., in the presence of potassium.

The starting salts of formula VIII may themselves be prepared by reacting the corresponding imidazoles, pyrazoles, triazoles and tetrazoles with a suitable acid.

The nature of the anion $X^-$ in the salts of formula VIII depends on the acid used in this step. The acids that may be used are, for example, those listed above and from which $X^-$ is derived.

Another method for synthesizing the salts of formula VIII in which A=B=C is described in U.S. Pat. No. 5,077,414.

This process comprises the reaction of an α-dicarbonyl compound X of formula:

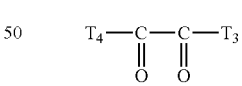

X in which $T_3$ and $T_4$ are as defined above, with HCHO and two amines of formulae. $T_1-NH_2$ and $T_2-NH_2$ in the presence of a suitable acid.

Other methods for preparing the salts of formula VIII are proposed in Chem. Eur. J. 1996, 2, n° 12, pages 1627–1636 and Angew. Chem. Int. Ed. Engl. 1997, 36, 2162–2187.

The compounds of formula IX may be prepared by condensing a suitable thiourea of formula XI:

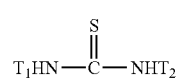

XI with an α-hydroxy ketone of formula XII:

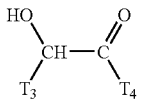

in which $T_1$, $T_2$, $T_3$ and $T_4$ are as defined above. Suitable operating conditions are described especially by N. Kuhn in Synthesis, 1993, 561.

According to one particularly preferred embodiment of the invention, the metallic complex of the invention has the formula:

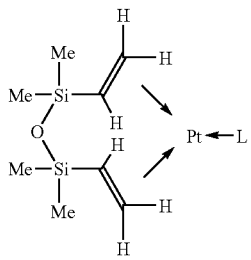

in which Lγ is as defined above.

A simple method for preparing this complex consists in reacting the carbene L with the Karstedt catalyst of average formula $Pt_2[ViMe_2Si\text{—}O\text{—}SiMe_2Vi]_3$ in which Vi represents a vinyl radical.

This reaction may be performed in bulk or in a solvent.

Examples of suitable solvents are cyclic or noncyclic ethers, such as diethyl ether, diisopropyl ether, tetrahydrofuran, dioxane, dimethoxyethane or diethylene glycol dimethyl ether; amides such as dimethylformamide or dimethylacetamide; and aromatic hydrocarbons (such as toluene or xylenes, but more particularly toluene).

Advantageously, the reaction is performed in an ether, and preferably in tetrahydrofuran.

The reaction temperature usually ranges between 10 and 50° C., preferably between 15 and 35° C. and very preferably between 20 and 25° C.

It is desirable to perform the process in the presence of a slight excess of carbene relative to the platinum. Thus, the molar ratio of the carbene L to platinum generally ranges between 1 and 1.3 and preferably between 1 and 1.1.

A simple way of performing the process consists in pouring, at a suitable temperature, a solution of the carbene in a solvent into a reactor containing a solution of the Karstedt catalyst in this same solvent.

The molarity of the carbene solutions and of the catalyst solution is not critical according to the invention.

According to one variant, this process consists essentially in placing the following in contact:
at least one salt of formula (VIII):

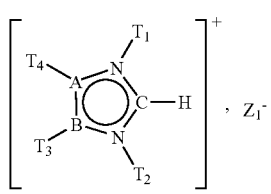

in which:

$A$, $B$, $T_1$, $T_2$, $T_3$ and $T_4$ are as defined above;

$Z_7$ independently represents an anion derived from a Brönsted acid (protic acid) preferably chosen from the group comprising:
carboxylic acids of formula Go-COOH in which Go represents an alkyl and advantageously a $C_1$–$C_{22}$ alkyl; an aryl, advantageously a $C_6$–$C_{18}$ aryl optionally substituted with one or more $C_1$–$C_6$ alkyl;
sulfonic acids of formula Go-$SO_3H$ in which Go is as defined above;
phosphoric acids of formula Go-$PO_3H$ in which Go is as defined above;
the following-mineral acids: HF, HCl, HBr, HI, $H_2SO_4$, $H_3PO_4$, $HClO_4$ and $HBF_4$, taken alone or in combination;
and mixtures thereof;
at least one precursor complex of formula (IVp) selected from the group comprising suitable precursor complexes (IVp) are the Karstedt complexes of formula:

$Pt_2[ViMe_2Si\text{—}O\text{—}SiMe_2Vi]_3$ in which Vi represents a vinyl radical;
at least one solvent (V);
and at least one base (VI).

Advantageously, the solvent V is chosen such that the solubility of the salt (VIII) and of the base (VI) in said solvent (V) is at least 1% weight/weight at 25° C., respectively.

The solvent (V) is chosen-from polar aprotic solvents with a boiling point at 1 atm of less than 150° C., preferably 120° C., preferentially from the group comprising:
cyclic or noncyclic ethers and in particular tetrahydrofuran (THF), diethyl ether, diisopropyl ether, dioxane, dimethoxyethane or diethylene glycol dimethyl ether;
dimethylformamide, dimethylacetamide, —hexamethylphosphorylamide: $[(CH_3)_2N]_3PO$ and hexamethylphosphoramide $[(CH_3)_2N]_3P$;
THF being particularly preferred.

The base(s) (VI) is (are) chosen from strong bases capable of deprotonating the salt (VIII), preferably from the group comprising:
alkali metal hydrides, alkali metal hydroxides,
alkali metal carboxylates, alkali metal alkoxides and alkali metal amides,
and even more preferably from the group comprising:
sodium hydride, sodium methoxide, potassium tert-butoxide and lithium diisopropylamide, and mixtures thereof;

The concentration of the base (VI) in the reaction medium, in M/1 of solvent (V), is preferably:

$$10^{-6} \leq VI \leq 1$$

and even more preferably $10^{-3} \leq VI \leq 10^{-1}$.

The salt (VIII) and the base (VI) are used in amounts such that the ratio $R_{VI/VIII}$ of normality VI/VIII is defined as follows:

$$R_{VI/VIII} \leq 1$$

preferably $1 \leq R_{VI/VIII} \leq 5$
and even more preferably $1 \leq R_{VI/VIII} \leq 3$.

In summary, this process consists essentially in:
a) dissolving the salt (VIII) and compound (IVp) in the solvent (V),
b) incorporating the base (VI) in several portions into the solution of (VIII) and (IVp) in (V),
c) stirring the reaction medium thus formed, preferably in the absence of light, until compound (I) has formed, d) recovering the formed compound (I), preferably by evaporation,
e) optionally, purifying,
f) optionally, drying.

Preferably, at least one of the steps a), b) and c), and preferentially all three of them, is (are) performed at a temperature of between 5 and 50° C., and preferably at room temperature.

The following are preferably used:
at least one salt (VIII) of formula:

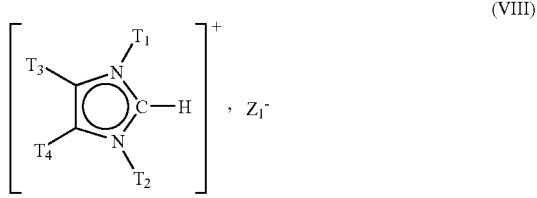

in which:
$T_1$ and $T_2$ are identical and represent $(C_1-C_8)$alkyl or $(C_3-C_8)$cycloalkyl;
$T_3$ and $T_4$ are identical and represent hydrogen or together represent a phenyl;
$Z_1$ is a halogen, preferably Cl or I, or $BF_4$;
at least one Karstedt complex as defined in patent U.S. Pat. No. 3,775,452, preferably a compound of formula (IVp):

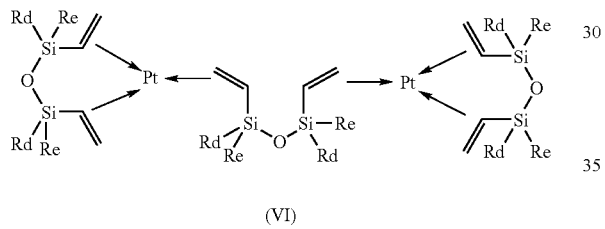

in which:
$R_d$ and $R_e$ are identical and represent $CH_3$;
a solvent (V) comprising THF;
and at least one base (VI) comprising potassium tert-butoxide (KOt-Bu).

The catalysts thus prepared may be used in hydrosilylation reactions. They allow homogeneous catalysis of the reaction.

They also give access to one-component silicone compositions, preferably of polyaddition EVC type, which have much longer pot lives than those prepared with standard platinum-based catalysts, this being achieved using little or no inhibitors -D-.

The invention is illustrated in the light of the examples that follow.

EXAMPLES

Example 1

1—Preparation of the Carbene of Formula:

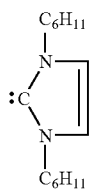

(cf. Chem. Eur. J. 1996, 2, 1627).

For this reaction, all the glassware used is oven-dried at 150° C. overnight and then cooled under argon.

The THF is distilled over sodium/benzophenone just before use.

A 100 ml three-necked flask is charged with 2.70 g (10 mmol) of 1,3-dicyclohexylimidazolinium chloride and then purged with a stream of argon, followed by suspending in 20 ml of THF. About 50 ml of ammonia are then condensed at −78° C. into the three-necked flask, resulting in the partial dissolution of the salt. The acetone/cardice bath is removed and 270 mg of 95% NaH (10.7 mmol, 1.07 eq.) are added slowly using a solids-addition funnel. Each addition of NaH is followed by a substantial evolution of gas ($H_2$) and the salt in suspension gradually dissolves. The reaction mixture is stirred for 1 hour 30 minutes at the reflux temperature of the solvent. The ammonia is then evaporated off and a pale yellow solution is obtained along with a solid in suspension (NaCl). This solution, the carbene concentration of which is 0.5 M in the THF, is used immediately to prepare the complexes.

2—Preparation of the Platinum Complex of Formula (Catalyst C1):

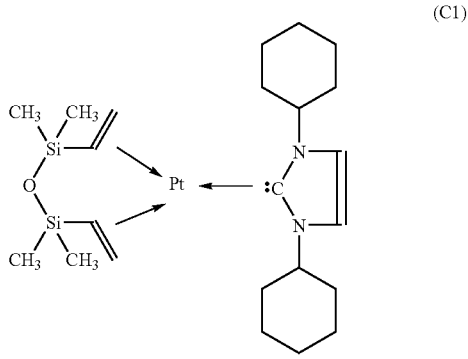

A Karstedt solution containing 10% by weight of platinum (i.e. 1.52 mmol of platinum) is prepared in accordance with the procedure described in U.S. Pat. No. 3,775,452.

3.2 ml of a 0.5 M solution of the carbene of formula:

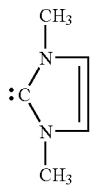

in tetrahydrofuran are added dropwise using a dropping funnel to 3 g of this solution, kept stirring and diluted in 10 ml of tetrahydrofuran. The addition is complete after 10 minutes. The reaction mixture is then stirred for 50 minutes at room temperature. Where appropriate, the light amount of insoluble material is filtered off and the reaction mixture is concentrated under vacuum.

After concentration, a pale yellow viscous residue is obtained. Over several hours, an abundant white solid precipitates from the residual divinyltetramethyldisiloxane. This solid is filtered off and washed with a few milliliters of hexamethyldisiloxane and then with pentane. 570 mg (60% yield) of an analytically pure white powder are thus obtained.

A fraction of this powder is recrystallized from a dichloromethane/absolute ethanol mixture. The resulting crystals are analyzed by X-ray diffraction. The analysis confirms the structure of the complex obtained.

Example 2

1—Preparation of the Carbene of Formula:

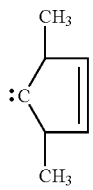

This carbene is prepared by performing the procedure illustrated in Example 1, paragraph 1, except that 2.7 g (10 mmol) of 1,3-dicyclohexylimidazolinium chloride are replaced with 2.3 g (10 mmol) of 1,3-dimethylimidazolinium iodide.

2—Preparation of the Platinum Complex of Formula C2:

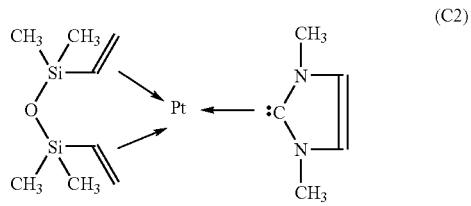
(C2)

This complex is prepared by performing the procedure of Example 1, except that the carbene used as starting material has the formula:

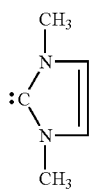

After concentrating, a yellow paste is obtained. This paste is filtered off and washed thoroughly with hot pentane. A whitish solid is isolated (35% yield), which is recrystallized from ethanol. The resulting crystals are analyzed by X-ray diffraction. The analysis confirms the structure of the complex obtained.

Example 3

Preparation of a Platinum Complex (III.2) of Formula (Catalyst C3):

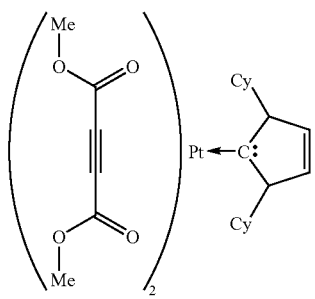
(C3)

500 mg (0.815 mmol) of the complex of Example 1 are placed in a 50 ml one-necked round-bottomed flask equipped with a magnetic stirrer. The flask is purged with a stream of argon. The complex is then dissolved in 25 ml of anhydrous THF. 116 μl (135 mg; 0.94 mmol; 5 eq.) of dimethyl acetylenedicarboxylate are then injected. The reaction mixture is maintained at the reflux temperature of the solvent for two hours. After cooling to room temperature, the THF is evaporated off under vacuum. The solid obtained is dissolved in the minimum amount of dichloromethane. The crude product is chromatographed on a column of silica (eluent: 80/20 cyclohexane/ethyl acetate). After concentrating under vacuum, the yellow flakes obtained are washed with 2-propanol and then suction-filtered. 350 mg. (60% yield) of an analytically pure yellow powder are obtained.

Example 4

Preparation of One-component Silicone Compositions Comprising the POSs -A- and -B- and the Catalysts -C1-, -C2- or -C3- of Examples 1, 2 and 3, Respectively In order to form a homogeneous phase with the silicone medium, the catalysts -C1-, -C2- and -C3- of Examples 1, 2 and 3 are introduced in solution in toluene. A base reaction system (M) is prepared by mixing together 100 grams of a polyorganovinylsiloxane containing 0.61% of vinyl by weight and 27 grams of a polyorganohydrogenosiloxane containing 0.17% by weight of hydrogen. For each example, the platinum is added to the mixture (M) in a proportion of 80 ppm by weight. Depending on the example, the nature of the catalyst and that of the inhibitor vary (tables 1 and 2 below). The Karstedt catalyst (platinum in oxidation state zero dissolved in a vinylsilicone oil) is taken as the reference system.

The inhibitors used are the following:

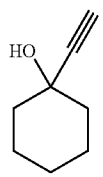
I1

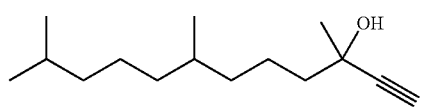
I2

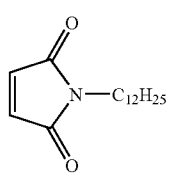
I3

Each system is evaluated by DSC and the gel time indicated corresponds to the time taken for the reaction mixture to set to a solid.

The results obtained are given in tables 1 and 2 below.

TABLE 1

| Test | Catalyst | Inhibitor | [Inh]/[Pt] | Onset Temp. (° C.) | Exotherm (° C.) | Tgel R.T. | Tgel 60° C. |
|---|---|---|---|---|---|---|---|
| 1 | C2 | / | / | 70 | 87 | 1 day | (i) |
| 2 | C1 | / | / | 75 | 111 | 1 day | (ii) |
| 3 | C2 | I1 | 60 | 144 | 148 | 40 days | 36 h |
| 4 | C2 | I2 | 60 | 145 | 147 | 40 days | 36 h |
| 5 | C1 | I1 | 60 | 137 | 149 | 40 days | 36 h |
| 6 | C1 | I2 | 60 | 141 | 149 | 40 days | 36 h |
| 7 | C1 | I3 | 60 | 142 | 149 | >40 days | (ii) |
| 8 | C3 | / | / | 115 | 130 | >40 days | (ii) |

(i) molar ratio between the inhibitor and the platinum
(ii) not measured

TABLE 2

| Counter test | Catalyst | Inhibitor | [Inh]/[Pt] (i) | Onset Temp. (° C.) | Exotherm (° C.) | Tgel R.T. | Tgel 60° C. |
|---|---|---|---|---|---|---|---|
| 1' | Karstedt | / | / |  | (ii) | qq min. | (iii) |
| 2' | Karstedt | I1 | 60 | 92 | 96 | 5 days | 5 h |
| 3' | Karstedt | I2 | 60 | 99.5 | 103.5 | 5 days | 5 h |
| 4' | Karstedt | I3 | 60 | 79 | 84 | 1 day | (ii) |

(i) molar ratio between the inhibitor and the platinum
(ii) not measured
(iii) not measurable due to excessively rapid crosslinking of the system Example 5

One-component EVC Silicone Composition According to the Invention (All the Parts are Given on a Weight Basis)

5.1: Preparation

The following reagents are mixed together for two hours at room temperature (23° C.) in a Z-arm mixing blender:
88 parts of a polyorganosiloxane, which is a poly(dimethyl)(methylvinyl)siloxane blocked at each of its two ends with a trimethylsiloxy unit, containing in the chain 720 ppm of Vi groups, with a viscosity of $5\times10^6$ mPa.s at 25° C.,
12 parts of a polyorganosiloxane, which is a poly(dimethyl)siloxane blocked at each of its two ends with a dimethylvinylsiloxy unit, containing 120 ppm of Vi groups, with a viscosity of $2\times10^6$ mPa.s at 25° C.,
43 parts of treated combustion silica $D_4$ with a specific surface area of 60 $m^2$/g,
2 parts of a polydimethylsiloxane oil blocked at its ends with dimethylhydroxysiloxy units, with a viscosity of 50 mPa.s at 25° C.

The following are added to this preparation, on cylinder:
2.82 parts of a poly(dimethyl)(methylhydro)siloxane oil blocked at each of its two ends with a dimethylhydrosiloxy unit, containing 45 000 ppm of H groups, with a viscosity of 300 mPa.s at 25° C.,
3.75 ppm of platinum metal supplied in the form of a platinum (0) complex,
225 ppm of an inhibitor of the SiH/SiVi addition reaction, which is diallyl maleate.

5.2: Characterization of the Composition:

A fraction of the homogeneous mass obtained is used to measure the mechanical properties of the silicone elastomer resulting from the hot vulcanization of the polyorganosiloxane composition. To do this, the fraction of the homogeneous mass retained for this purpose is then vulcanized for 10 minutes at 170° C., working in a suitable mold allowing plaques 2 mm thick to be obtained. Plaques in nonannealed (NA) form are obtained. A fraction of the plaques then undergoes annealing (or aging) (A) for four hours at 200° C. Standardized samples are then taken from these plaques as a whole and the following properties are measured:

Shore A hardness (SAH) according to standard DIN 53505
Breaking strength (BS) in MPa according to AFNOR standard NF T 46002
Elongation at break (EB) in % according to the above standard
100% modulus of elasticity (ME) in MPa according to the above standard.

Another fraction of the homogeneous mass obtained from the blender is used to measure the change in the Williams plasticity of the nonvulcanized silicone elastomer as a function of the storage time and of the temperature.

5.3: Results

Mechanical Properties

The results are given in table 3 below:

TABLE 3

|  | Characteristics | Nonannealed | Annealed 4 h/200° C. |
|---|---|---|---|
| Karstedt Pt counterexample | SAH | 46 | 56 |
|  | BS (MPa) | 7.2 | 8.0 |
|  | EB (%) | 602 | 522 |
|  | 100% ME (MPa) | 1.4 | 1.8 |
| Catalyst of example 1: Pt/cyclohexyl carbene | SAH | 47 | 58 |
|  | BS (MPa) | 7.9 | 8.7 |
|  | EB (%) | 722 | 542 |
|  | 100% ME (MPa) | 1.2 | 1.8 |

Comments:

The composition according to the invention gives an elastomer whose mechanical properties are slightly higher than those obtained with a standard composition, without Pt catalyst/cyclohexyl carbene, but with Karstedt Pt.

Williams Plasticity

The results are given in table 4 below.

TABLE 4

| | Characteristics | 25° C. | 50° C. |
|---|---|---|---|
| Karstedt Pt counterexample | Time (days) | 38 | 2 |
| | % increase in consistency | 100 | 100 |
| Catalyst of example 1: Pt/cyclohexyl carbene | Time (days) | 80 | 8 |
| | % increase in consistency | 66 | 100 |

Comments:

The pot life of the composition according to the invention is markedly longer than that obtained with a standard composition, without Pt catalyst/cyclohexyl carbene, but with Karstedt Pt.

The invention claimed is:

1. A hydrosilylation-crosslinkable silicone composition comprising at least one polyorganosiloxane -A- (POS) bearing ethylenic and/or acetylenic unsaturation(s), at least one polyorganohydrogenosiloxane -B-, in the presence of a metallic catalyst -C- and optionally comprising at least one inhibitor -D- of the hydrosilylation reaction;

wherein the catalyst -C- comprises at least one compound selected from the products of formula (I):

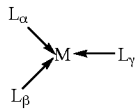

(I)

in which

M is a metal selected from Pt, Pd and Ni in oxidation state 0;

$L_\gamma$ represents a carbene of formula (II):

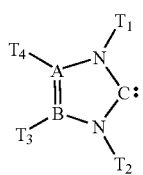

II in which:

A and B independently represent C or N, it being understood that when A represents N, then $T_4$ represents nothing, and when B represents N, then $T_3$ represents nothing;

$T_3$ and $T_4$ independently represent a hydrogen atom; an alkyl group; a cycloalkyl group optionally substituted with alkyl or alkoxy; an aryl group optionally substituted with alkyl or alkoxy; an alkenyl group; an alkynyl group; or an arylalkyl group in which the aryl portion is optionally substituted with alkyl or alkoxy;

or alternatively $T_3$ and $T_4$ may form, together with A and B when these each represent a carbon atom, an aryl;

$T_1$ and $T_2$ independently represent an alkyl group; an alkyl group optionally substituted with alkyl; a perfluorinated alkyl group or an alkyl group optionally substituted with a perfluoroalkyl group; a cycloalkyl group optionally substituted with alkyl or alkoxy; an aryl group optionally substituted with alkyl or alkoxy; an alkenyl group; an alkynyl group; or an arylalkyl group in which the aryl portion is optionally substituted with alkyl or alkoxy; or alternatively $T_1$ and $T_2$ independently represent a monovalent radical of formula (V) below:

$$V_1\text{-}V_2 \qquad (V)$$

in which:

$V_1$ is a divalent hydrocarbon-based radical, $V_2$ is a monovalent radical selected from the following group of substituents:

alkoxy, —OR° with R° corresponding to hydrogen, alkyl or aryl amine, or $T_1$ and $T_2$ independently represent a monovalent radical of formula (W) below:

$$W_1\text{-}\omega\text{-}W_2 \qquad (W)$$

in which:

$W_1$ is, a divalent hydrocarbon-based radical, optionally substituted linear or branched $C_1$–$C_{10}$ alkylene, ω represents:

—R¹C═CR¹— with R¹ corresponding to H or alkyl or

—C≡C—

$W_2$ is a monovalent radical selected from the group of the following substituents $R^2$=alkyl, H;

Si-substituted with alkyl or Si-substituted with alkoxy, alcohol, ketone, carboxyl, amide, acyl, or alternatively the substituents $T_1$, $T_2$, $T_3$ and $T_4$ may form in pairs, when they are located on two adjacent ring members in formula (II), a saturated or unsaturated hydrocarbon-based chain;

$L_\alpha$ and $L_\beta$ are ligands that may be identical or different, and each represent:

(III.1)

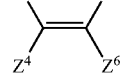

(III.2)

with, in these formulae (III.1) and (III.2):

$Z^1, Z^2, Z^3, Z^4, Z^5, Z^6$ each independently representing:
a. hydrogen,
b. a halogen,
c. a cyano,
d. a saturated or unsaturated electron-withdrawing hydrocarbon-based group, optionally adjacent to the double or triple bond,
e. two vicinal $Z^{1\ to\ 6}$ together optionally forming an electron-withdrawing ring optionally different than the carbene $L_\gamma$ of formula (II) and optionally comprising hetero atoms;

or the substituents $Z^1$ and $Z^2$ together form, in (III. 1), a divalent alkenyl radical comprising at least one electron-withdrawing residue optionally adjacent to the triple bond;

or alternatively $Z^3$ to $Z^6$ form in pairs, in (III.2), a divalent alkenyl radical comprising at least one electron-withdrawing residue optionally adjacent to the double bond;

or together form the ligand $L\delta$ of formula (IV):

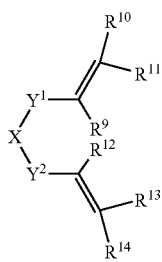

(IV)

in which:

$Y_1$ and $Y_2$ represent, independently of each other, $CR_aR_b$ or $SiR_cR_d$;

X represents O, $NR_e$ or $CR_fR_g$;

$R^{10}$, $R^{11}$, $R^{13}$ and $R^{14}$, which may be identical or different, are selected from a hydrogen atom, an alkyl group and an aryl group optionally substituted with alkyl;

$R^9$, $R^{12}$, $R_a$, $R_b$, $R_c$ and $R_d$ are selected independently from a hydrogen atom; an alkyl group; an acyl group; an aryl group optionally substituted with alkyl; a cycloalkyl group optionally substituted with alkyl; and an arylalkyl group in which the aryl portion is optionally substituted with alkyl;

$R_e$ is H or alkyl; or alternatively when $Y_1$ and $Y_2$ independently represent $SiR_cR_d$, two groups $R_c$ linked to two different silicon atoms together form a chain of formula:

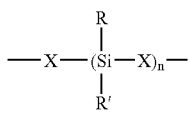

in which n is an integer from 1 to 3; X is as defined above; R and R', which may be identical or different, take any of the meanings given above for $R_e$, it being understood that when n is 2 or 3, only one silicon atom of said chain may be substituted with one or two alkenyl or alkynyl groups; or alternatively when $Y_1$ and $Y_2$ independently represent $SiR_cR_d$, two groups $R_c$ linked to different silicon atoms together form a saturated hydrocarbon-based chain, the two groups $R_c$ together with said silicon atoms and X forming a 6- to 10-membered ring; or alternatively when $Y_1$ and $Y_2$ independently represent $CR_aR_b$, two groups $R_a$ linked to different carbon atoms together form a saturated hydrocarbon-based chain, the two groups $R_a$ together with the carbon atoms that bear them and X form a 6- to 10-membered ring; and $R_f$ and $R_g$ represent, independently of each other, a hydrogen atom; an alkyl group; an acyl group; an aryl group optionally substituted with alkyl; a cycloalkyl group optionally substituted with alkyl; an arylalkyl group in which the aryl portion is optionally substituted with alkyl; a halogen atom; an alkenyl group; an alkynyl group; or a group $SiG_1G_2G_3$ in which $G_1$, $G_2$ and $G_3$ are, independently of each other, alkyl; alkoxy; aryl optionally substituted with alkyl or alkoxy; or arylalkyl in which the aryl portion is optionally substituted with alkyl or alkoxy.

2. The composition as claimed in claim 1 wherein, in formula (II):

$T_3$ and $T_4$ represent a hydrogen atom or together form a phenyl, and/or $T_1$ and $T_2$, which may be identical or different, represent $(C_1-C_8)$alkyl or $(C_3-C_8)$cycloalkyl, wherein the group of radicals comprising: methyl, n-propyl, n-pentyl, neopentyl ($-CH_2-C(CH_3)_3$), cyclopentyl, cyclohexyl, adamantyl, allyl ($-CH_2-CH=CH_2$), methallyl ($-CH_2-C(CH_3)=CH_2$), propargyl, homopropargyl ($-(CH_2)_2-C\equiv CH$), or

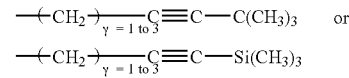

or alternatively: $-(CH_2)_{\gamma=1\ to\ 4}$-amine or $-(CH_2)_{\gamma=1\ to\ 4}$-alkoxy;

and/or A and B both represent a carbon atom.

3. The composition as claimed in claim 1, wherein, in formulae (III.1) and (III.2), the electron-withdrawing residues are selected from the group consisting of:

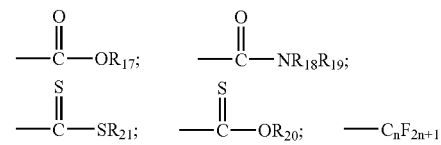

in which:

$R_{17}$, $R_{18}$, $R_{19}$ and $R_{20}$ are a substituted or unsubstituted alkyl, alkenyl, alkynyl or trialkylsilyl, and n is between 1 and 50.

4. The composition as claimed in claim 1, wherein:

$Z^1$, $Z^2$, $Z^3$, $Z^4$, $Z^5$ and $Z^6$ are selected from the group comprising:

$-COOH_3$, $-COOCH_2CH_3$, $-CONC_{12}H_{25}$, or and, in the case where the substituents $Z^1$ and $Z^2$ form, in pairs and with the triple bond, in (III.1), a ring Cy1 and where $Z^3$ to $Z^6$ form in pairs, with or without the double bond, in (III.2), a ring Cy2, these rings Cy1 and Cy2 are independently selected from the group consisting of the following rings:

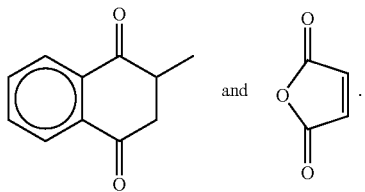 and

5. The composition as claimed in claim 1, wherein X represents O; $Y_1$ and $Y_2$ independently represent $SiR_dR_e$.

6. The composition as claimed in claim 1, wherein $R^{10}$, $R^{11}$, $R^{13}$ and $R^{14}$ are hydrogen atoms.

7. The composition as claimed in claim 1, wherein $R^9$ and $R_{12}$ represent a hydrogen atom; an alkyl group; an aryl group optionally substituted with alkyl; or a cycloalkyl group optionally substituted with alkyl.

8. The composition as claimed in claim 1, wherein, in the ligands Lδ of formula (IV) of the catalyst -C-:
   when X represents O, $Y_1$ and $Y_2$ independently represent $SiR_cR_d$; or
   when X represents $NR_e$, $Y_1$ and $Y_2$ independently represent $CR_aR_b$; or
   when X represents $CR_fR_g$, $Y_1$ and $Y_2$ independently represent $CR_aR_b$.

9. The composition as claimed in claim 1, wherein $R^9=R^1$; $R^{10}=R^{13}$; $R^{11}=R^{14}$ and either $Y^1=CR_aR_b$ and $Y^2=CR_aR_b$ in which $R_a$ and $R^b$ together form a symmetrical chain, or alternatively $Y^1=SiR_cR_d$ and $Y^2=SiR_cR_d$ in which $R_c$ and $R^d$ together form a symmetrical chain.

10. The composition as claimed in claim 1, wherein the catalyst -C- corresponds to formula (I.1) below:

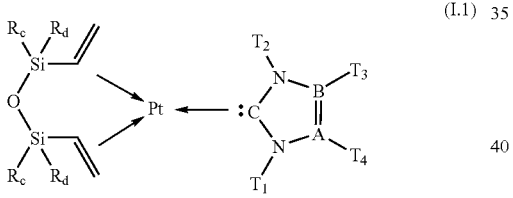

(I.1)

in which:
   $T_1$ and $T_2$ are identical and represent $(C_1-C_8)$alkyl or $(C_3-C_8)$cycloalkyl;
   $T_3$ and $T_4$ are as defined in claim 1;
   $R_c$ and $R_d$ are as defined in claim 1.

11. The composition as claimed in claim 1, wherein the catalyst -C- is selected from the metallic complexes of formula (I.2) below:

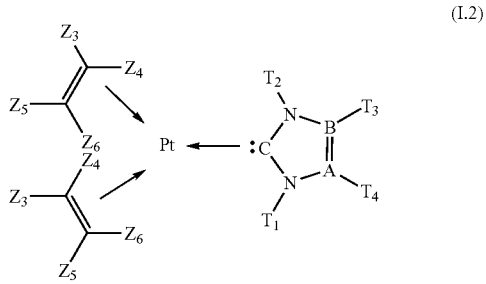

(I.2)

in which:
   $Z_3$ and $Z_6$ are as defined in claim 1;
   $T_1$ and $T_2$ are identical and are as defined in claim 1;
   $T_3$ and $T_4$ are as defined in claim 1.

12. The composition as claimed in claim 1, wherein the catalyst -C- is selected from the metallic complexes of formula (I.3) below:

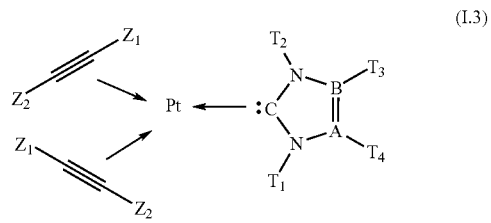

(I.3)

in which:
   $Z_1$ and $Z_2$ are as defined in claim 1;
   $T_1$ and $T_2$ are identical and are as defined in claim 1;
   $T_3$ and $T_4$ are as defined above.

13. The composition as claimed in claim 1, wherein the POSs -A- and -B- are selected from the group consisting of siloxyl units of general formula:

$(R^{20})_xSiO_{4-x/2}$      (I')

and of siloxyl units of formula:

$(R^{21})_y(R_{22})_zSiO_{4-y-z/2}$      (II')

in which formulae the various symbols have the following meaning:
   the symbols $R^{20}$ and $R^{22}$, which may be identical or different, each represent a nonhydrolyzable hydrocarbon group, this radical optionally being:
      an alkyl or haloalkyl radical comprising from 1 to 5 carbon atoms and, when in the from of a haloalkyl, comprising from 1 to 6 chlorine and/or fluorine atoms,
      cycloalkyl and halocycloalkyl radicals containing from 3 to 8 carbon atoms and, when in the from of a haloalkyl, comprising from 1 to 4 chlorine and/or fluorine atoms,
      aryl, alkylaryl and haloaryl radicals containing from 6 to 8 carbon atoms and, when in the from of a haloalkyl, comprising from 1 to 4 chlorine and/or fluorine atoms,
      cyanoalkyl radicals containing 3 or 4 carbon atoms;
   the symbols $R^{21}$, which may be identical or different, each represent a hydrogen atom, a $C_2-C_6$ alkenyl group, a hydroxyl group, a hydrolyzable atom or a hydrolyzable group;
   x=an integer-equal to 0, 1, 2 or 3;
   y=an integer equal to 0, 1, 2 or 3;
   z=an integer equal to 0, 1 or 2;
   the sum y+z is between 1 and 3;
with the condition that a POS -A- Si-alkenyl comprises at least one unit $R^{21}$=alkenyl per molecule and a POS -B- Si—H comprises at least one unit $R^{21}$=hydrogen per molecule;
   optionally
   $R^{20}$ methyl; ethyl; propyl; isopropyl; butyl; isobutyl; n-pentyl; t-butyl; chloromethyl; dichloromethyl; α-chloroethyl; α,β-dichloroethyl; fluoromethyl; difluoromethyl; α,β-difluoroethyl; 3,3,3-trifluoropropyl; trifluorocyclopropyl; 4,4,4-trifluorobutyl; 3,3,4,4,5,5-hexafluoropentyl; β-cyanoethyl; γ-cyanopropyl; phenyl; p-chlorophenyl; m-chlorophenyl; 3,5-dichlorophenyl; trichlorophenyl; tetrachlorophenyl; o-, p- or m-tolyl; α,α,α-trifluorotolyl; xylyls optionally 2,3-dimethylphenyl, 3,4-dimethylphenyl;

$R^{21}$=hydrogen or vinyl.

14. The composition as claimed in claim 1, wherein the crosslinking inhibitors are selected from:
polyorganosiloxanes, which are optionally cyclic, substituted with at least one alkenyl, or tetramethylvinyltetrasiloxane,
unsaturated amides,
alkyl, alkenyl or alkynyl maleates, or diallyl maleate,
acetylenic alcohols,
alkyl, alkenyl or alkynyl acetylenedicarboxylates,
and combinations thereof.

15. The composition as claimed in claim 1, which comprises at least one crosslinking inhibitor -D- and at least one catalyst and wherein at least one of the substituents $Z_1$ to $Z_6$ of this (or these) catalyst(s) -C- comprise(s) at least one electron-withdrawing residue.

16. The composition as claimed in claim 1, which is free of crosslinking inhibitor -D-, and comprises at least one catalyst and wherein this (or these) catalyst(s) -C- comprise(s) substituents $Z_1$ to $Z_6$ free of electron-withdrawing residues.

17. A metallic complex of formula I as defined in claim 1, wherein:
the carbene ligand $L_\gamma$ of formula (II) is such that:
$T_3$ and $T_4$ can form, together with A and B when these each represent a carbon atom, an aryl as defined above, optionally a phenyl;
and/or $T_1$ and $T_2$ independently represent a monovalent radical of formula (V) below:

$V_1$-$V_2$     (V)

in which:
$V_1$ is a divalent hydrocarbon-based radical,
$V_2$ is a monovalent radical selected from the following group of substituents:
alkoxy, —$OR^\circ$ with $R^\circ$ corresponding to hydrogen, alkyl or aryl
amine,
and/or $T_1$ and $T_2$ independently represent a monovalent radical of formula (W) below:

$W_1$-ω-$W_2$     (W)

in which:
$W_1$ is a divalent hydrocarbon-based radical, optionally substituted linear or branched $C_1$–$C_{10}$ alkylene,
ω represents:

—$R^1C$=$CR^1$— with $R_1$ corresponding to H or alkyl or

—C≡C—

$W_2$ is a monovalent radical selected from the group of the following substituents
$R^2$=alkyl, H;
Si-substituted with alkyl or Si-substituted with alkoxy;
alcohol;
ketone
carboxyl,
amide,
acyl $T_1$ and $T_2$ optionally independently corresponding to a radical W of the type

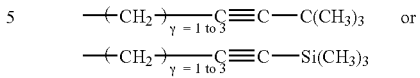

or alternatively to one of the following units:
methyl, isopropyl, tert-butyl, n-pentyl, neopent.yl, cyclopentyl, cyclohexyl, adamantyl, allyl, methallyl, propargyl or homopropargyl, or alternatively
the substituents $T_1$, $T_2$, $T_3$ and $T_4$ can form in pairs, when they are located on two adjacent ring members in formula (II), a saturated or a unsaturated hydrocarbon-based chain.

18. The metallic complex of formula (I) as claimed in claim 17, having the following formula:

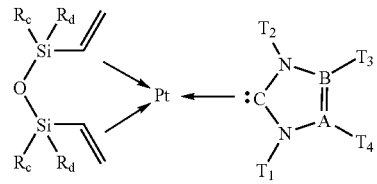

in which:
$T_1$ and $T_2$ are identical and represent $(C_1$–$C_8)$alkyl or $(C_3$–$C_8)$cycloalkyl;
$T_1$ and $T_2$ are as defined in claim 1;
$R_c$ and $R_d$ are as defined in claim 1.

19. A catalytic composition comprising, as active material, one or more metallic complexes as claimed in claim 17.

20. The silicone composition of claim 17, wherein when $T_1$ and $T_2$ independently represent a monovalent radical of formula (V) and $V_2$=an amine, the amine is $N(R^\circ)_2$ with $R^\circ$ corresponding to hydrogen, alkyl or aryl.

21. The silicone composition of claim 17, wherein when $T_1$ and $T_2$ independently represent a monovalent radical of formula (W) and $W_2$ is $Si(R^3)_3$ with $R^3$=alkyl.

22. The silicone composition of claim 17, wherein when $T_1$ and $T_2$ independently represent a monovalent radical of formula (W) and $W_2$ is an alcohol, the alcohol is $C(R^4)_2OH$ with $R^4$=H or alkyl.

23. The silicone composition of claim 17, wherein when $T_1$ and $T_2$ independently represent a monovalent radical of formula (W) and $W_2$ is a ketone, the ketone is

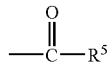

with $R^5$=alkyl.

24. The silicone composition of claim 17, wherein when $T_1$ and $T_2$ independently represent a monovalent radical of formula (W) and $W_2$ is a carboxyl, the carboxyl is

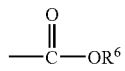

with $R^6$=alkyl.

25. The silicone composition of claim 17, wherein when $T_1$ and $T_2$ independently represent a monovalent radical of formula (W) and $W_2$ is an amide, the amide is

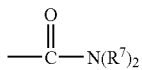

with $R^7$=H, alkyl.

26. The silicone composition of claim 17, wherein when $T_1$ and $T_2$ independently represent a monovalent radical of formula (W) and $W_2$ is an acyl, the acyl is

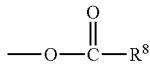

with $R^8$=alkyl.

27. A metallic complex of formula (I) as defined in claim 1 in which:
  $L_\gamma$ is as defined in claim 1
  $L\alpha$ and $L\beta$ independently correspond to the compounds of (III.1) or (III.2) as defined in claim 1.

28. The metallic complex of formula (I) as claimed in claim 27, of formula (I) below:

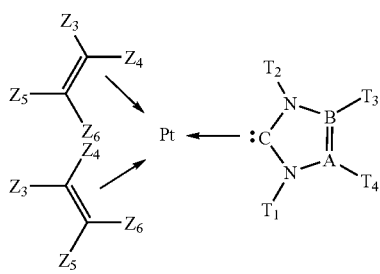

in which:
  $T_1$ and $T_2$ are identical and are as defined above;
  $T_3$ and $T_4$ are as defined above;
  $Z_3$ and $Z_6$ are as defined in claim 1 above.

29. The metallic complex of formula (I) as claimed in claim 27, of formula (I) below:

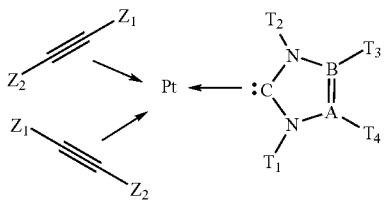

in which:
  $T_1$ and $T_2$ are identical and are as defined above;
  $T_3$ and $T_4$ are as defined above;
  $Z_1$ and $Z_2$ are as defined in claim 1.

30. A process for the hydrosilylation of olefins or acetylenic derivatives, comprising using the silicone composition and the catalytic composition as claimed in claim 1.

31. A process for the hydrosilylation of olefins or acetylenic derivatives comprising using the composition as claimed in claim 1 comprising at least one inhibitor -D- and, allowing the in situ formation of at least one metallic complex.

32. The silicone composition of claim 1, wherein when $T_1$ and $T_2$ independently represent a monovalent radical of formula (V) and $V_2$=an amine, the amine is $N(R^\circ)_2$ with $R^\circ$ corresponding to hydrogen, alkyl or aryl.

33. The silicone composition of claim 1, wherein when $T_1$ and $T_2$ independently represent a monovalent radical of formula (W) and $W_2$ is $Si(R^3)_3$ with $R^3$=alkyl.

34. The silicone composition of claim 1, wherein when $T_1$ and $T_2$ independently represent a monovalent radical of formula (W) and $W_2$ is an alcohol, the alcohol is $C(R^4)_2OH$ with $R^4$=H or alkyl.

35. The silicone composition of claim 1, wherein when $T_1$ and $T_2$ independently represent a monovalent radical of formula (W) and $W_2$ is a ketone, the kethone is

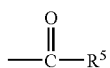

with $R^5$=alkyl.

36. The silicone composition of claim 1, wherein when $T_1$ and $T_2$ independently represent a monovalent radical of formula (W) and $W_2$ is a carboxyl, the carboxyl is

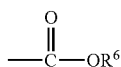

with $R^6$=alkyl.

37. The silicone composition of claim 1, wherein when $T_1$ and $T_2$ independently represent a monovalent radical of formula (W) and $W_2$ is an amide, the amide is

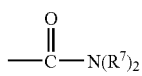

with $R^7$=H, alkyl.

38. The silicone composition of claim 1, wherein when $T_1$ and $T_2$ independently represent a monovalent radical of formula (W) and $W_2$ is an acyl, the acyl is

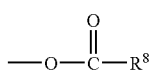

with $R^8$=alkyl.

* * * * *